US010278395B2

(12) United States Patent
Velev et al.

(10) Patent No.: US 10,278,395 B2
(45) Date of Patent: May 7, 2019

(54) FUNCTIONALIZED ENVIRONMENTALLY BENIGN NANOPARTICLES

(71) Applicant: North Carolina State University, Raleigh, NC (US)

(72) Inventors: Orlin D. Velev, Raleigh, NC (US); Alexander P. Richter, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 772 days.

(21) Appl. No.: 14/202,259

(22) Filed: Mar. 10, 2014

(65) Prior Publication Data

US 2014/0256545 A1 Sep. 11, 2014

Related U.S. Application Data

(60) Provisional application No. 61/776,274, filed on Mar. 11, 2013.

(51) Int. Cl.
*A01N 25/26* (2006.01)
*A01N 59/16* (2006.01)

(52) U.S. Cl.
CPC .................................. *A01N 59/16* (2013.01)

(58) Field of Classification Search
CPC ...................................................... A01N 59/16
USPC ......................................................... 504/100
See application file for complete search history.

(56) References Cited

U.S. PATENT DOCUMENTS

| 3,594,201 | A | * | 7/1971 | Sommer et al. ...... C08L 95/005 106/14.21 |
| 4,532,269 | A | | 7/1985 | Gitlitz et al. |
| 4,957,557 | A | | 9/1990 | Dimitri |
| 5,192,361 | A | | 3/1993 | Schilling |
| 5,919,487 | A | | 7/1999 | Simonnet et al. |
| 7,951,853 | B2 | | 5/2011 | Ismail et al. |
| 7,973,096 | B2 | | 7/2011 | Anderson et al. |
| 8,097,270 | B2 | | 1/2012 | Ketelson et al. |
| 8,148,484 | B2 | | 4/2012 | Gstrein et al. |
| 8,282,944 | B2 | | 10/2012 | Youngs et al. |
| 8,314,078 | B2 | | 11/2012 | Mousa et al. |
| 8,409,627 | B2 | | 4/2013 | Richardson et al. |
| 8,425,926 | B2 | | 4/2013 | Qiu et al. |
| 8,454,986 | B2 | | 6/2013 | De Windt et al. |
| 8,460,759 | B2 | | 6/2013 | Leach et al. |
| 8,512,417 | B2 | | 8/2013 | Miller et al. |
| 8,603,534 | B2 | | 12/2013 | Zale et al. |
| 2003/0216326 | A1 | * | 11/2003 | Alimi ..................... A61K 31/70 514/22 |
| 2004/0115424 | A1 | * | 6/2004 | Cowton ................... C08J 7/047 428/327 |
| 2004/0247690 | A1 | | 12/2004 | Yang |
| 2005/0037050 | A1 | * | 2/2005 | Weber ....................... A61F 2/04 424/426 |
| 2005/0226938 | A1 | | 10/2005 | Borbely et al. |
| 2007/0243259 | A1 | * | 10/2007 | Sung .................... A61K 9/5146 424/489 |
| 2007/0244569 | A1 | * | 10/2007 | Weber ....................... A61F 2/07 623/23.75 |
| 2010/0020333 | A1 | | 1/2010 | Kunz et al. |
| 2010/0056399 | A1 | * | 3/2010 | Berkland ............... C09K 8/516 507/201 |
| 2010/0210616 | A1 | | 8/2010 | Youngs et al. |
| 2010/0247908 | A1 | | 9/2010 | Velev et al. |
| 2010/0280452 | A1 | * | 11/2010 | Chen ..................... A61L 29/085 604/103.01 |
| 2011/0111957 | A1 | | 5/2011 | Ishaque et al. |
| 2011/0135742 | A1 | | 6/2011 | Kim et al. |
| 2011/0257006 | A1 | | 10/2011 | Thieuleux et al. |
| 2011/0263037 | A1 | | 10/2011 | Herz et al. |
| 2012/0190593 | A1 | * | 7/2012 | Soane ....................... C09K 8/03 507/111 |
| 2012/0195947 | A1 | * | 8/2012 | Perumal ................. A61K 31/07 424/401 |
| 2013/0196450 | A1 | | 8/2013 | Van Hoonacker et al. |
| 2013/0338049 | A1 | * | 12/2013 | King ..................... C10M 159/02 508/181 |

FOREIGN PATENT DOCUMENTS

| EP | 0 429 723 A1 | 6/1991 |
| WO | WO 2007/092029 A2 | 8/2007 |
| WO | WO 2008/100163 | 8/2008 |
| WO | WO 2012/058627 A2 | 5/2012 |
| WO | WO 2012/140252 A1 | 10/2012 |
| WO | WO 2012/150890 | 11/2012 |
| WO | WO 2012/161603 | 11/2012 |

(Continued)

OTHER PUBLICATIONS

Bio-Based Polymers and Composites, p. 565, obtained online on Nov. 14, 2016 via www.books.google.com.*

(Continued)

*Primary Examiner* — Mina Haghighatian
*Assistant Examiner* — Mei Ping Chui
(74) *Attorney, Agent, or Firm* — Olive Law Group, PLLC

(57) ABSTRACT

This invention is directed to the preparation and applications of internally and/or externally functionalized environmentally benign nanoparticles (EbNPs), which are produced by a three step procedure: (1) synthesis of native EbNPs, (2) functionalization with active agents, and (3) additional surface property customization via one or more modifier(s).

9 Claims, 15 Drawing Sheets

(56) References Cited

FOREIGN PATENT DOCUMENTS

WO    WO 2013/133706 A1 *   9/2013

OTHER PUBLICATIONS

Richter AP et al. An environmentally benign antimicrobial nanoparticle based on a silver-infused lignin core. Nature Nanotechnology 10: 817-823 (Jul. 13, 2015) doi: 10.1038/nnano.2015.141.
Richter AP et al. Supplementary Information: An environmentally benign antimicrobial nanoparticle based on a silver-infused lignin core. Nature Nanotechnology 10: S1-S24 (Jul. 13, 2015). doi: 10.1038/nnano.2015.141.
Product Data Bulletin: Indulin® AT kraft pine lignin. MeadWestvaco Corporation Specialty Chemicals, Charleston, SC. 2 pp.
Material Safety Data Sheet: Indulin® AT, version: 3. MeadWestvaco Corporation Specialty Chemicals Division, North Charleston, SC. 7 pp.
Adair et al., "Resistance of *Pseudomonas* to Quaternary Ammonium Compounds. I. Growth in Benzalkonium Chloride Solution", *Appl. Microbiol.*, 1969, vol. 18(3), pp. 299-302.
Ahamed et al., "Silver nanoparticle applications and human health", *Clinica Chimica Acta*, 2010, vol. 411, pp. 1841-1848.
Arora et al., "Cellular responses induced by silver nanoparticles: In vitro studies", *Toxicology Letters*, 2008, vol. 179, pp. 93-100.
Arora et al., "Interactions of silver nanoparticles with primary mouse fibroblasts and liver cells", *Toxicology and Applied Pharmacology*, 2009, vol. 236, pp. 310-318.
Barakat et al., "Characterization of arabinoxylan-dehydrogenation polymer (synthetic lignin polymer) nanoparticles", *Biomacromolecules*, 2007, vol. 8(4), pp. 1236-1245.
Bystrzejewska-Piotrowska et al., "Nanoparticles: Their potential toxicity, waste and environmental management", *Waste Management*, 2009, vol. 29, pp. 2587-2595.
Capek et al., *145 Advances in Polymer Science, Radical Polymerisation Polyelectrolytes*, Springer-Verlag, Berlin Heidelberg, 1999, 203 pages.
Carmeli et al., "Health and Economic Outcomes of Antibiotic Resistance in *Pseudomonas aeruginosa*", *Arch. Intern. Med.*, May 24, 1999; vol. 159, pp. 1127-1132.
Chakar et al., "Review of current and future softwood kraft lignin process chemistry", *Industrial Crops and Products*, 2004, vol. 20, pp. 131-141.
Cohen et al., "Nonchromosomal Antibiotic Resistance in Bacteria: Genetic Transformation of *Escherichia coli* by R-Factor DNA*", *Proc, Nat. Acad. Sci.*, Aug. 1972, vol. 69, No. 8, pp. 2110-2114.
Cohen, Mitchell L., "Epidemiology of Drug Resistance: Implications for a Post-Antimicrobial Era", *Science*, New Series, Aug. 21, 1992, vol. 257, No. 5073, pp. 1050-1055.
Davies et al., "The Involvement of Cell-to-Cell Signals in the Development of a Bacterial Biofilm", *Science*, 1998, vol. 280, pp. 295-298.
De Moura et al., "Development of cellulose-based bactericidal nanocomposites containing silver nanoparticles and their use as active food packaging", *J Food Eng* 2012, vol. 109(3), pp. 520-524.
El Badawy et al., "Surface Charge-Dependent Toxicity of Silver Nanoparticles", *Environ. Sci. Technol.*, 2011, vol. 45, pp. 283-287.
Feng et al., "A mechanistic study of the antibacterial effect of silver ions on *Escherichia coli* and *Staphylococcous aureus*", 2000, Wiley & Sons, Inc., 7 pages.
Frangville et al., "Fabrication of Environmentally Biodegradable Lignin Nanoparticles", *ChemPhysChem*, 2012, vol. 13, pp. 4235-4243.
Gosheger et al., "Silver-coated megaendoprostheses in a rabbit model—an analysis of the infection rate and toxicological side effects", *Biomaterials*, 2004, vol. 25, pp. 5547-5556.
Harmita et al., "Copper and cadmium sorption onto kraft and organosolv lignins", *Bioresource Technology*, 2009, vol. 100, pp. 6183-6191.
Hassellov et al., "Nanoparticle analysis and characterization methodologies in environmental risk assessment of engineered nanoparticles", *Ecotoxicology*, 2008, vol. 17, pp. 344-361.
Heitz et al., "Fractionation of Populus tremuloides at the Pilot Plant Scale: Optimization of Steam Pretreatment Conditions using the STAKE II Technology", *Bioresource Technology*, 1991, vol. 35, pp. 23-32.
Hu et al., "Synthesis and characterization of chitosan—poly (acrylic acid) nanoparticles", *Biomaterials*, 2002, vol. 23(15), pp. 3193-3201.
International Search Report and the Written Opinion of the International Searching Authority corresponding to International Application No. PCT/US14/22382, dated Jun. 18, 2014; 15 pages.
Jain et al., "Potential of Silver Nanoparticle-Coated Polyurethane Foam as an Antibacterial Water Filter", *Biotechnology and Bioengineering*, Apr. 5, 2005; vol. 90, No. 1, pp. 59-63.
Jain et al., *The Handbook of Nanomedicine, Second Edition*, Springer Science+Business Media, New York, 2012, 562 pages.
Klasen et al., "A historical review of the use of silver in the treatment of burns. II. Renewed interest for silver", *Burns*, 2000, vol. 26, pp. 131-138.
Klibanov, Alexander M., "Permanently microbicidal materials coatings", *J. Mater. Chem.*, 2007, vol. 17, pp. 2479-2482.
Kulthong et al. "Determination of silver nanoparticle release from antibacterial fabrics into artificial sweat", *Particle and Fibre Toxicology*, 2010, vol. 7:8, 9 pages.
Kumar et al., "Silver-nanoparticle-embedded antimicrobial paints based on vegetable oil" *Nature Materials*, Mar. 2008, vol. 7(3), 236-241.
Kvítek et al., "Effect of Surfactants and Polymers on Stability and Antibacterial Activity of Silver Nanoparticles (NPs)", *J. Phys. Chem. C*, 2008, vol. 112, pp. 5825-5834.
Langsrud et al., "Intrinsic and acquired resistance to quaternary ammonium compounds in food-related *Pseudomonas* spp.", *Journal of Applied Microbiology*, 2003, vol. 95, pp. 874-882.
Lee et al., "Antibacterial effect of nanosized silver colloidal solution on textile fabrics", *Journal of Materials Science*, 2003, vol. 38, pp. 2199-2204.
Liau et al., "Interaction of silver nitrate with readily identifiable groups: relationship to the antibacterial action of silver ions", *Letters in Applied Microbiology*, 1997, vol. 25, pp. 279-283.
Liu et al., "Adsorption of Heavy Metal Ion from Aqueous Single Metal Solution by Aminated Epoxy-Lignin", *BioResources*, 2013, vol. 8(2), pp. 2257-2269.
Liyama et al., "Covalent Cross-Links in the Cell Wall", *Plant Physiol.*, 1994, vol. 104, pp. 315-320.
Liz-Marzán et al., "Reduction and Stabilization of Silver Nanoparticles in Ethanol by Nonionic Surfactants", *Langmuir*, 1996, vol. 12, No. 15, pp. 3585-3589.
Lora et al., "Recent Industrial Applications of Lignin: A Sustainable Alternative to Nonrenewable Materials", *Journal of Polymers and the Environment*, Apr. 2002, vol. 10, Nos. 1/2, pp. 39-48.
Luoma et al., "Silver Nanotechnologies and the Environment: Old Problems or New Challenges?", *Project on Emerging Nanotechnologies 15*, Woodrow Wilson International Center for Scholars and The PEW Charitable Trusts, Sep. 2008, 72 pages.
Matsumura et al., "Mode of Bactericidal Action of Silver Zeolite and Its Comparison with That of Silver Nitrate", *Applied and Environmental Microbiology*, 2003, vol. 69(7), pp. 4278-4281.
Morones et al., "The bactericidal effect of silver nanoparticles", *Nanotechnology*, 2005, vol. 16, pp. 2346-2353.
Neal, Andrew L., "What can be inferred from bacterium—nanoparticle interactions about the potential consequences of environmental exposure to nanoparticles?", *Ecotoxicology*, 2008, vol. 17, pp. 362-371.
Ohashi et al., "Antibacterial activity of silver inorganic agent YDA filler", *Journal of Oral Rehabilitation*, 2004, vol. 31, pp. 364-367.
Paddle-Ledinek et al., "Effect of Different Wound Dressings on Cell Viability and Proliferation", *Plastic & Reconstructive Surgery*, Jun. 2006, vol. 117, Issue 7S, pp. 110S-118S.

(56) References Cited

OTHER PUBLICATIONS

Pal et al., "Does the Antibacterial Activity of Silver Nanoparticles Depend on the Shape of the Nanoparticle? A Study of the Gram-Negative Bacterium *Escherichia coli*", *Appl. Environ. Microbiol.*, 2007, vol. 73(6), pp. 1712-1720.

Panáček et al., "Silver Colloid Nanoparticles: Synthesis, Characterization, and Their Antibacterial Activity", *J. Phys. Chem. B*, 2006, vol. 110, pp. 16248-16253.

Poole et al., "Multiple Antibiotic Resistance in Pseudomonas aeruginosa: Evidence for Involvement of an Efflux Operon", *J. Bacteriology*, 1993, vol. 175(22), pp. 7363-7372.

Popa et al., "Nanoparticles based on modified lignins with biocide properties", *Cellulose Chemistry and Technology*, 2011, vol. 45(3-4), pp. 221-226.

Qi et al., "Preparation and antibacterial activity of chitosan nanoparticles", Carbohydrate Research, 2004, vol. 339, pp. 2693-2700.

Rai et al., "Silver nanoparticles as a new generation of antimicrobials", *Biotechnology Advances*, 2009, vol. 27, pp. 76-83.

Raveendran et al., "Completely "Green" Synthesis and Stabilization of Metal Nanoparticles", *J. Am. Chem. Soc.*, 2003, vol. 125, pp. 13940-13941.

Samuel et al., "Prevention of catheter-related infections: the potential of a new nano-silver impregnated catheter", *International Journal of Antimicrobial Agents*, 2004, 23S1, pp. S75-S78.

Stern et al., "Nanotechnology Safety Concerns Revisited", *Toxicological Sciences*, 2008, vol. 101(1), pp. 4-21.

Tan et al., "Synthesis of Positively Charged Silver Nanoparticles via Photoreduction of $AgNO_3$ in Branched Polyethyleneimine/HEPES Solutions", *Langmuir*, 2007, vol. 23, pp. 9836-9843.

Walser et al., "Persistence of engineered nanoparticles in a municipal solid-waste incineration plant", Nature Nanotechnology, Aug. 2012, vol. 7, pp. 520-524.

Xiu et al., "Negligible Particle-Specific Antibacterial Activity of Silver Nanoparticles", *Nano Lett.*, 2012, vol. 12, pp. 4271-4275.

Zhang et al., "Facile synthesis of spherical cellulose nanoparticles", *Carbohydrate Polymers*, 2007, vol. 69, pp. 607-611.

Zhao et al., "Bacteria-removing and Bactericidal Efficiencies of PDADMAC Composite Coagulants in Enhanced Coagulation Treatment", *Clean Soil Air Water Journal*, 2013, vol. 41(1), pp. 37-42.

\* cited by examiner

FUNCTIONALIZED ENVIRONMENTALLY BENIGN NANOPARTICLES

STATEMENT REGARDING FEDERALLY SPONSORED RESEARCH OR DEVELOPMENT

This invention was made with government support under Grant No. 554,871 awarded by the U.S. Environmental Protection Agency. The government has certain rights in the invention.

1. FIELD OF THE INVENTION

This invention relates generally to the preparation and applications of internally and/or externally functionalized environmentally benign nanoparticles (EbNPs), which are produced by a three-step procedure: (1) synthesis of native EbNPs, (2) functionalization with active agents, and (3) additional surface property customization via one or more modifier(s).

2. BACKGROUND OF THE INVENTION

2.1. Introduction

Engineered nanoparticles exhibit unique and useful physical, chemical, and biological particle-specific attributes that may help to solve pressing challenges of mankind in industries including life sciences, energy, and health care. However, nanoparticle waste has been recognized as a potential health hazard,[1] as the post-utilization activity of engineered nanoparticles combined with their persistence may result in short and long-term toxicity in humans and the environment.[2] For example, it has been found that the physical and chemical characteristics of persistent nanoparticles (PNPs), and therefore, their activity, may not change even after high-temperature treatments in solid-waste incineration plants.[3] One way to minimize the post-utilization hazard of nanoparticles is to minimize their residence time and presence in the environment. Employing degradable nanoparticles with matching functionality to PNPs may serve as a suitable solution.

Lignin, the most abundant aromatic polymer in nature,[4] has an amorphous structure and is biodegradable. Lignin covalently crosslinks the cell walls of plants, and plays a vital role in plant health, growth, and development.[5] When extracted from biomass, the structure of modified lignin varies depending on the initial plant source and the method of isolation. Lignin obtained via the organosolv process, such as High Purity Lignin (HPL), is strongly hydrophobic, does not incorporate any sulfur containing groups, and therefore, preserves best the structure of native lignin of all processed lignins.[6] However, the most common extraction method is the Kraft pulping processes.[7] INDULIN AT lignin (IAT), a modified lignin that contains a small number of hydrophilic thiol groups, is recovered by this process. In aqueous systems, matrixes of IAT have shown high absorbance capabilities of heavy metal ions for environmental remediation purposes.[8,9] Cationic metal ions are electrostatically attracted to IAT, which is negatively charged in aqueous solution due to deprotonation of its main functional groups (Table 6). Recently, the synthesis of pH-stable IAT-based environmentally benign nanoparticles (EbNPs) in ethylene glycol was reported.[10] Hence, we propose that by infusing IAT EbNPs with functional metal ions, it will be possible to synthesize degradable nanoparticles that match the nanoparticle functionality of the respective metal PNPs, while increasing post-utilization safety.

Silver nanoparticles (AgNPs) are among the most widely employed PNPs, as their broad-spectrum antimicrobial properties allow them to combat bacteria strains exhibiting antibiotic resistance,[11] which are reported in human pathogens including *Escherichia coli* (*E. coli*)[12] and *Pseudomonas aeruginosa* (*P. aeruginosa*).[13] As infection control measures can minimize the spread of drug-resistant bacteria,[14] and therefore the potential for nosocomial infections,[15] silver-containing products may find increasing utilization in the medical sector to prevent bacteria growth on catheters,[16] prostheses,[17] and dental materials,[18] and to reduce the infection potential of burn wounds.[19] In addition, with the emergence of antimicrobial PNPs in textiles,[20] water filters,[21] and other consumer products, the human exposure potential to PNPs with their associated risks increases. Human skin exposure studies indicate that AgNPs can be released from antibacterial fabrics into liquids resembling "sweat".[22] Studies on commercially available wound dressings proved that dressings containing AgNPs exhibit stronger cytotoxic effects toward keratinocytes than do PNP-free counterparts.[23] In vitro studies on mammalian fibroblasts have revealed that AgNP can induce apoptosis. In this context, AgNP may potentially affect human health.[24,25,26]

Several methods for the preparation of antimicrobial silver-based nanoparticle systems have been reported. Most procedures employ highly reactive reducing agents such as sodium borohydride ($NaBH_4$) or hydrazine ($N_2H_4$) to reduce silver ions to metallic silver. Green synthesis methods of producing AgNP can reduce the environmental impact during fabrication given that no harsh solvents or reducing agents are employed.[27,28] However, due to the persistent nature of AgNPs, the problem of post-utilization toxicity associated with non-degradable nanoparticles remains unaddressed.

3. SUMMARY OF THE INVENTION

In particular non-limiting embodiments, the present invention provides:
1. A nanoparticle comprising:
   a biodegradable biopolymer core, an antiviral or cytotoxic agent loaded on the biodegradable core, and a cationic layer coating the biodegradable core with the bioactive agent.
2. The nanoparticle of claim 1, wherein the biodegradable biopolymer core is either a lignin, a modified lignin, or a linear, branched, or cross-linked polysaccharide.
3. The nanoparticle of claim 1, wherein the biodegradable biopolymer core is a plant- or animal-derived biopolymer.
4. The nanoparticle of claim 3, wherein the plant- or animal-derived biopolymer core is a cellulose, a chitin, a chitosan, a hemicellulose, a lignocellulose, a modified cellulose, a modified chitosan, a modified lignin, a protein, or a combination thereof.
5. The nanoparticle of claim 4, wherein the chitosan is a medium or high molecular weight chitosan or a derivative thereof.
6. The nanoparticle of claim 4, wherein the modified cellulose is cellulose acetate, cellulose nitrate, cellulose propionate, ethyl cellulose, hydroxyethyl cellulose, hydroxypropyl methylcellulose phthalate, hydroxypropyl methylcellulose acetate succinate, or methyl cellulose, or a derivative thereof.

7. The nanoparticle of claim 4, wherein the modified chitosan is a low molecular weight chitosan, a chitosan with amino groups in the backbone, or a derivative thereof.

8. The nanoparticle of claim 4, wherein the modified lignin is sulfonated or unsulfonated lignin.

9. The nanoparticle of claim 1, wherein the antiviral or cytotoxic agent is an antiviral agent.

10. The nanoparticle of claim 1, wherein the antiviral or cytotoxic agent is a biocide, a cationic metal, a catalyst, a fumigant, a herbicide, a pesticide, a photocatalyst, or a semiconductor.

11. The nanoparticle of claim 10, wherein the biocide is an algaecide, a bactericide, or a fungicide.

12. The nanoparticle of claim 11, wherein the fungicide is captan, chlorothalonil, cyrodinil, folpet, mepanipyrim, pyrimethanil, sulfur, or vinclozolin.

13. The nanoparticle of claim 11, wherein the fungicide is an ethylenebisdithiocarbamate or a natural fungicide.

14. The nanoparticle of claim 13, wherein the ethylenebisdithiocarbamate is mancozeb, maneb, metiram, nabam, or zineb.

15. The nanoparticle of claim 13, wherein the natural fungicide is *ampelomuces quisqualis*, cinnamaldehyde, cinnamon essential oil, jojoba oil, monocerin, neem oil, rosemary oil, or tee tree oil.

16. The nanoparticle of claim 10, wherein the cationic metal is $Ag^+$, $Ag^{2+}$, $Ag^{3+}$, $Co^{2+}$, $Cu^{2+}$, $Fe^{2+}$, $Ni^{2+}$, or $Zn^{2+}$.

17. The nanoparticle of claim 10, wherein the fumigant is 1,3-dichloropropene, chloropicrin, formaldehyde, iodoform, metam sodium, methyl bromide, methyl iodide, methyl isocyanate, phosphine, or sulfuryl fluoride.

18. The nanoparticle of claim 10, wherein the herbicide glyphosate, triclopyr, 1,1'-dimethyl-4,4'-bipyridinium ion (paraquat) or a chemical derivative, analogue or salt thereof.

19. The nanoparticle of claim 10, wherein the herbicide is a chloracetanilide herbicide, glyphosate herbicide, an imidazolinone herbicide, an organic herbicide, a phenoxy herbicide, a phenylurea herbicide, a triazine herbicide, or a triazolopyrimidine herbicide.

20. The nanoparticle of claim 19, wherein the chloracetanilide herbicide is acetochlor, alachlor, butachlor, metolachlor, or propachlor.

21. The nanoparticle of claim 19, wherein the imidazolinone herbicide is imazapyr, imazamethabenz-methyl, imazapic, imazethapyr, imazamox or imazaquin.

22. The nanoparticle of claim 19, wherein the organic herbicide is corn gluten meal, vinegar, D-limonene, or monocerin.

23. The nanoparticle of claim 19, wherein the phenoxy herbicide is 2,4-Dichlorophenoxyacetic acid, 2,4,5-Trichlorophenoxyacetic acid, 2-Methyl-4-chlorophenoxyacetic acid, 2-(2-Methyl-4-chlorophenoxy)propionic acids, 2-(2,4-Dichlorophenoxy)propionic acid, or 2,4-Dichlorophenoxy)butyric acid.

24. The nanoparticle of claim 19, wherein the phenylurea herbicide is N'-(3,4-dichlorophenyl)-N,N-dimethylurea (diuron), 1,1-dimethyl-3-[3-(trifluoromethyl)phenyl (flumeturon), or N,N-dimethyl-N'-[4-(1-methylethyl)phenyl (isoproturon).

25. The nanoparticle of claim 19, wherein the triazine herbicide is ametryn, atrazine, cyanazine, prometon, prometryn, propazine, simazine, terbuthylazine, or terbutryn.

26. The nanoparticle of claim 19, wherein the triazolopyrimidine herbicide is clorasulam-methyl, diclosulam, florasulam, flumetsulam, metosulam, penoxsulama, or pyroxsulama.

27. The nanoparticle of claim 10, wherein the pesticide is an avicide, an insecticide, a miticide, a molluscicide, a nematicide, or a rodenticide.

28. The nanoparticle of claim 27, wherein the insecticide is a carbamate or a pyrethroid insecticide.

29. The nanoparticle of claim 28, wherein the carbamate insecticide is aldicarb, carbaryl, carbofuran, formentanate, methiocarb, oxamyl, pirimicarb, propoxur, or thiodicarb.

30. The nanoparticle of claim 28, wherein the pyrethroid insecticide is allethrin, bifenthrin, cyhalothrin, lambda-cyhalothrin, cypermethrin, cyfluthrin, deltamethrin, etofenprox, fenvalerate, permethrin, phenothrin, prallethrin, pesmethrin, tetramethrin, tralomethrin, or transfluthrin.

31. The nanoparticle of claim 27, wherein the rodenticide is an anticoagulants, brodifacouma, bromadiolonea, chlorophacinone, difethialone, diphacinone, pindone, warfarin, nonanticoagulant, bromethalin, cholecalciferol, strychnine, or zinc phosphide 32. The nanoparticle of claim 10, wherein the semiconductor is $Ag_2S$, $CdS$, $CdSe$, $CdTe$, $Cu_2S$, $CuCl$, $CuO$, $Fe_2O_3$, $Fe_2S$, $Fe_3O_4$, $FeO$, $NiO$, $TiO_2$, $ZnO$, $ZnS$, $ZnSe$, or $ZnTe$.

33. The nanoparticle of claim 1, wherein the bioadhesive layer is a cationic polymer.

34. The nanoparticle of claim 33, wherein the cationic polymer is a polyamino-polymer.

35. The nanoparticle of claim 34, wherein the polyamino-polymer is branched polyethyleneimine (BPEI), polyallylamine hydrochloride (PAH), polydiallyldimethylammonium chloride (PDADMAC), polyethoxylated tallow amine (POEA), polyethyleneimine (PEI), or polylysine.

36. The nanoparticle of claim 1, wherein the bioadhesive layer comprises primary, secondary, tertiary, or quaternized amines.

37. The nanoparticle in claim 1, where the bioadhesive layer comprises carbohydrates, polypeptides, lectins, proteins, or antibodies or other molecules or materials with affinity to microbes, viruses or seeds.

38. The nanoparticle in claim 1, where the bioadhesive layer comprises nanohairs, nanolatches 39. The nanoparticle of claim 1, wherein the nanoparticle has a diameter of about 10 nm to about 500 nm.

40. The nanoparticle of claim 39, wherein the nanoparticle has a diameter of about 20 nm to about 100 nm.

41. The nanoparticle of claim 40, wherein the nanoparticle has a diameter of about 50 nm to about 80 nm.

42. A coated article comprising a surface wherein at least a portion of the surface is coated with the nanoparticle of claim 1.

43. The coated article of claim 42, wherein the coated article is an air filter, an article of clothing, an article of hygiene, a building material, a face mask, a food stuff package, a medical device, or a seed.

44. The coated article of claim 43, wherein the medical device is bandage, a biological implant, a dressing, a medical scaffold, a surgical instrument, or a wound covering.

45. The use of the nanoparticle of claim 1 to impart antiviral or cytotoxic properties to a substrate.

46. A method for fabricating a nanoparticle, the method comprising:
contacting a solvent containing a dissolved biodegradable biopolymer with an anti-solvent so as to form a biodegradable biopolymer core;
loading an antiviral or cytotoxic agent on the biopolymer core; and coating the biopolymer core and the antiviral or cytotoxic agent with a bioadhesive layer.

47. A method for fabricating a nanoparticle, the method comprising:
altering the pH of a suitable solvent containing a dissolved biodegradable biopolymer so as to form a biodegradable biopolymer core;
loading an antiviral or cytotoxic agent on the biopolymer core; and
coating the biopolymer core and the antiviral or cytotoxic agent with a bioadhesive layer.

48. A method for fabricating a nanoparticle, the method comprising:
contacting an organic solvent containing a dissolved biodegradable biopolymer with an aqueous solvent under suitable pH conditions so as to form a biodegradable biopolymer core;
loading an antiviral or cytotoxic agent on the biopolymer core; and
coating the biopolymer core and the antiviral or cytotoxic agent with a bioadhesive layer.

49. A method for fabricating a nanoparticle, the method comprising:
contacting an aqueous containing a dissolved biodegradable biopolymer with a polyelectrolyte under suitable conditions so as to form a biodegradable biopolymer core;
loading an antiviral or cytotoxic agent on the biopolymer core; and
coating the biopolymer core and the antiviral or cytotoxic agent with a bioadhesive layer.

50. A nanoparticle fabricated according to the method of claim 46.
51. A nanoparticle fabricated according to the method of claim 47.
52. A nanoparticle fabricated according to the method of claim 48.
53. A nanoparticle fabricated according to the method of claim 49.
54. The nanoparticle of claim 4, wherein the protein is a prolamin or a gluten
55. The nanoparticle of claim 54, wherein the prolamin is gliadin, hordein, secalin, zein, kafirin or avenin.
56. The nanoparticle of claim 54, wherein the gluten is gladin or glutenin.
57. The nanoparticle of claim 1, wherein the biodegradable biopolymer core is a byproduct of lignin degradation.
58. The nanoparticle of claim 57, wherein the byproduct of lignin degradation is humic acid.

4. DETAILED DESCRIPTION OF THE INVENTION

4.1. Concept

Section 1

Figure 1:
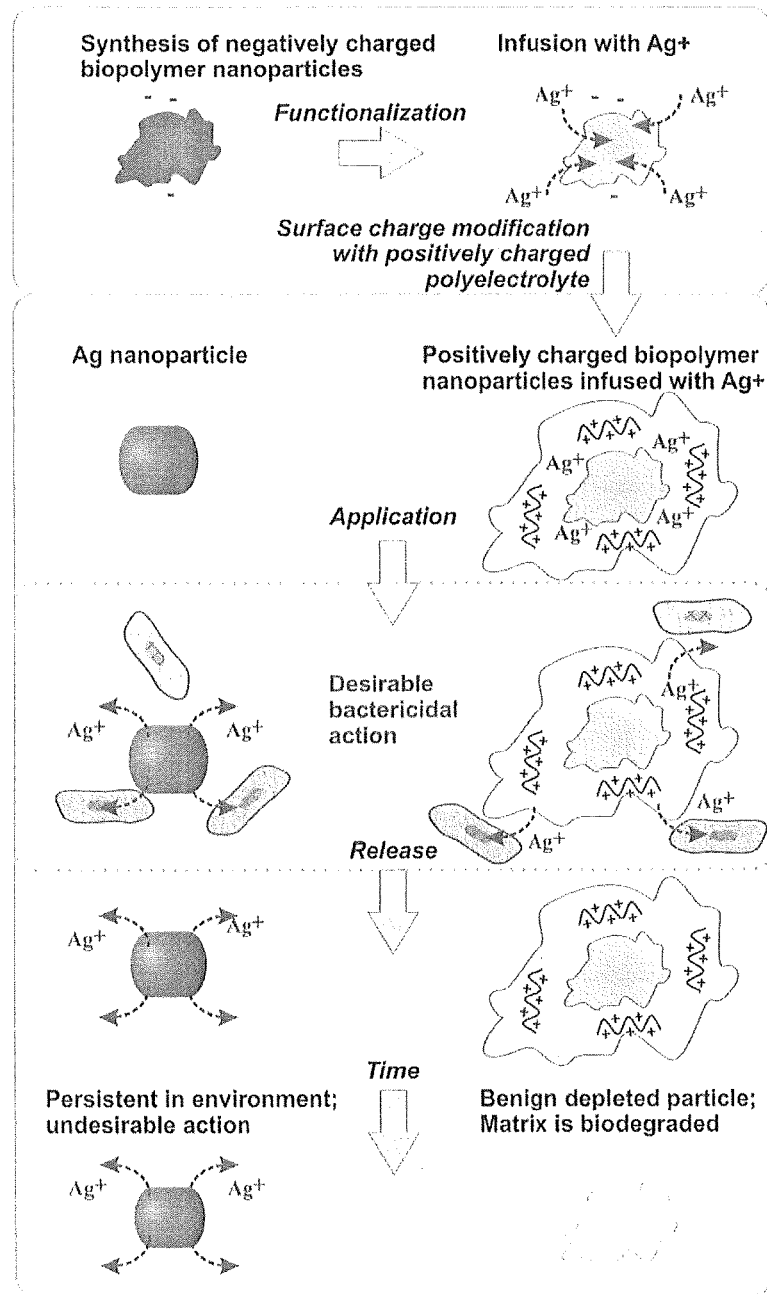
FIG. 1: Schematic of the concept for making and using environmentally benign bactericidal nanoparticles (EbNPs) compared to the present use of AgNPs.

The schematic in FIG. 1 illustrates the three steps involved in generating sustainable antimicrobial nanoparticles, and their life cycle in comparison to that of persistent AgNPs. In one, non-limiting embodiment, the silver ion infused lignin-based EbNPs with positive surface charge consist of: (1) a biodegradable EbNP core (negatively charged IAT EbNPs); (2) an active agent (antimicrobial silver ions adsorb on the negatively charged EbNP core); and (3) a surface modifier (polydiallyldimethylammonium chloride [PDADMAC], a positively charged polyelectrolyte). Both systems can attach to negatively charged bacteria cells. Both systems can release silver ions, which perform the desired antimicrobial function leading to bacteria cell death. When examining the silver release from the AgNP system, first metallic silver has to dissolve before it can be released in its ionic form into the bacteria. As the change of state from metallic to ionic silver may limit the rate at which silver ions are transferred from the AgNP system to the cell, this may reduce, overall, the antimicrobial efficiency of the system. In contrast to the metallic silver in AgNPs, ionic silver is already available in Ag-EbNPs-PDADMAC at contact with the cell. Therefore, Ag-EbNPs-PDADMAC may be capable of releasing silver ions more readily. This may result in high antimicrobial efficiency and rapid Ag depletion of the Ag-EbNPs-PDADMAC system. At the end of the lifecycle, both systems may eventually be released into the environment as nanomaterial waste. Moreover, as AgNPs may stay active, releasing reactive silver ions post-utilization, they represent persistent nanoparticle waste that could result in hazards for humans and the environment. On the other hand, the Ag-EbNPs-PDADMAC system, which is depleted of silver ions, is rendered inactive and will degrade over time; hence, Ag-EbNPs-PDADMAC may increase post-utilization safety for humans and the environment.

Here, we report non-limiting, exemplary data on the synthesis of native HPL and IAT EbNPs, the infusion of native IAT EbNPs with silver ions, the surface charge modification of the system with PDADMAC, and the quantification of antimicrobial efficiencies for opportunistic human pathogens *E. coli* and *P. aeruginosa*. In addition, we provide a hypothesis to explain the antimicrobial mechanism associated with Ag-EbNPs-PDADMAC.

1. RESULTS

1.1 Synthesis and Characterization of HPL EbNPs

Figure 2:
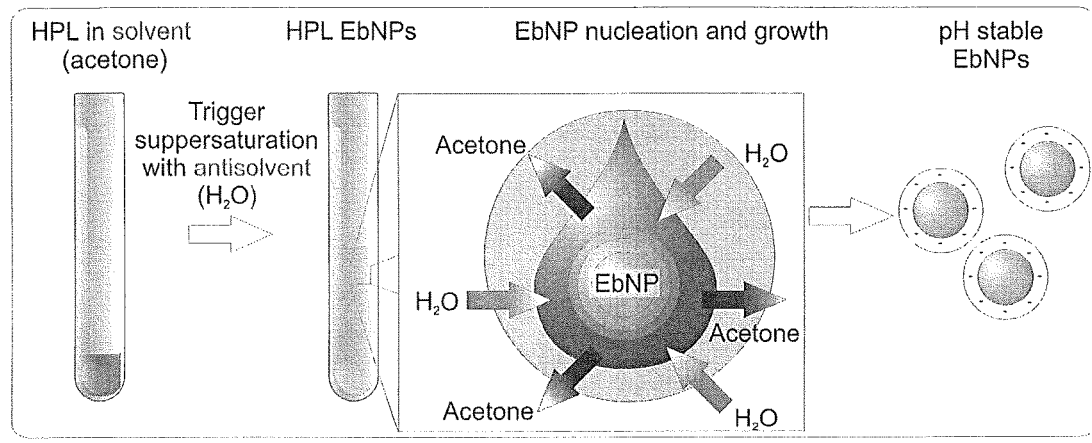
FIG. 2: Schematics of the concept for synthesizing HPL EbNP via the solvent-antisolvent method.

We synthesized native HPL EbNPs via the solvent-antisolvent precipitation method. As illustrated in FIG. 2, hydrophobic HPL is first dissolved in a good solvent, which is acetone, and rapidly transferred into an antisolvent, which is Millipore $H_2O$. Upon change of media, HPL may precipitate out as stable negatively charged EbNPs. The main parameters controlling the size and size distribution of these EbNPs include the initial HPL loading in the solvent, and the rate of dilution with antisolvent.

Figure 3:
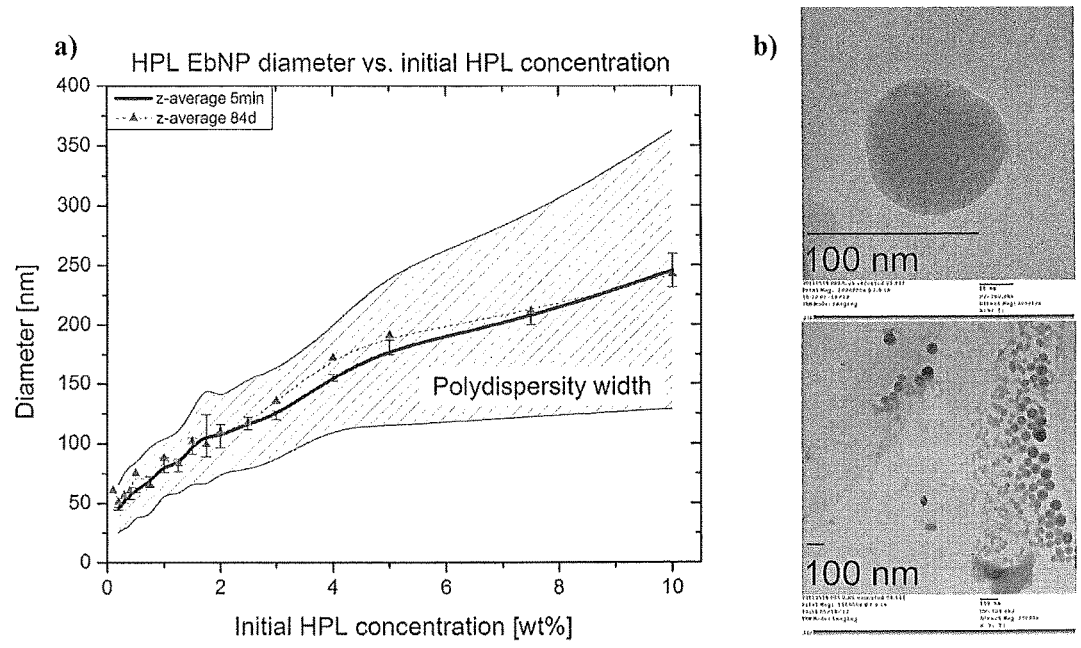
FIG. 3: HPL EbNP synthesis. a) size as a function of initial HPL concentration in solvent. b) TEM micrographs of native HPL EbNP.

The data on the effect of the initial HPL loading in the solvent on the final EbNP size are shown in FIG. 3. The TEM images may indicate spherical particles with diameters below 100 nm. The preparation of the samples included the following two steps (1) 1 ml of HPL dissolved in acetone was placed in a 20 ml scintillation vial, (2) 9.21 ml of Millipore $H_2O$ was rapidly added to the solution immediately precipitating out HPL EbNPs. The samples obtained were then further diluted to 0.05 wt %, which is a suitable concentration for size measurements with dynamic light scattering (DLS). The EbNP z-average diameters increased with increasing amount of HPL in the initial solvent. Repeated testing, as indicated with error bars, shows that the target diameters are reproducible. While the polydispersity width increases with particle size, the polydispersity indexes, which fluctuate mainly between 0.05 and 0.20, did not show a distinct trend. The wide polydispersity width observed could be a consequence of the broad molecular weight size distribution of the raw material HPL. The stability of the particle suspensions over time was confirmed with a size measurement performed after 84 days, which did not show any significant change in diameter.

1.1.1 HPL EbNP Dilution Rate Study

Figure 4:
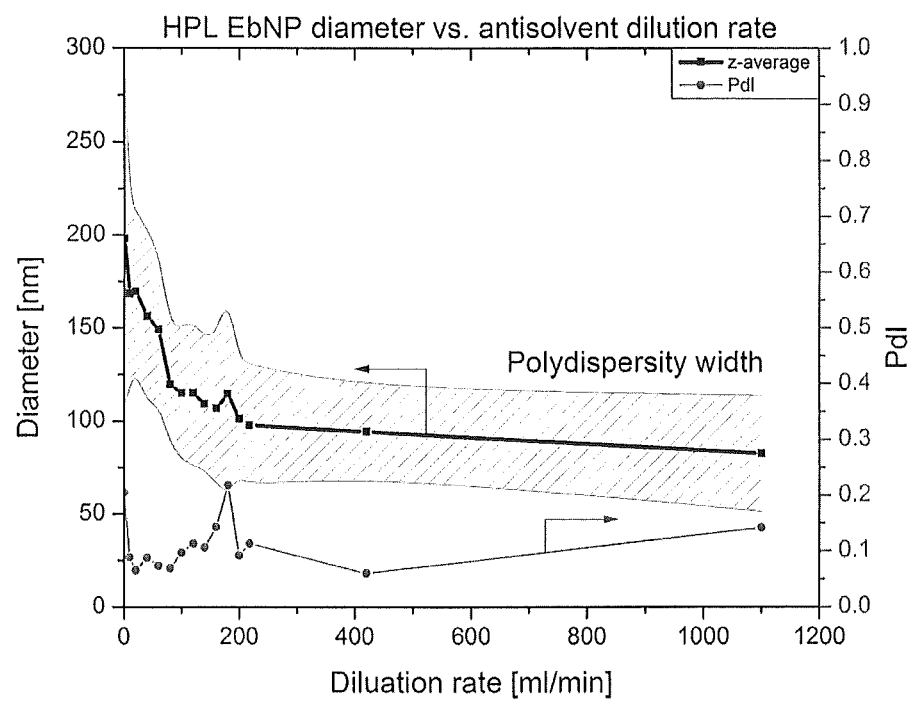
FIG. 4: HPL EbNP size as a function of antisolvent dilution rate.

We investigated the effect of the stock solution dilution rate on the HPL EbNP size. As reported in FIG. 4, the particle size decreases with increasing dilution rate. Up to a dilution rate of 218 ml/minute, the rate was adjusted with a syringe pump. For the dilution rates that could not be achieved with a syringe pump, the ones at 420 ml/minute and 1100 ml/minute, we utilized a 10 ml hand pipette and performed a video analysis on the pipette tip to calculate the actual dilution rate. Overall, we developed a facile method to synthesize pH-stable HPL EbNPs with size control in the range of 50 to 250 nm in diameter.

1.1.2 HPL EbNP pH Stability

Figure 5:
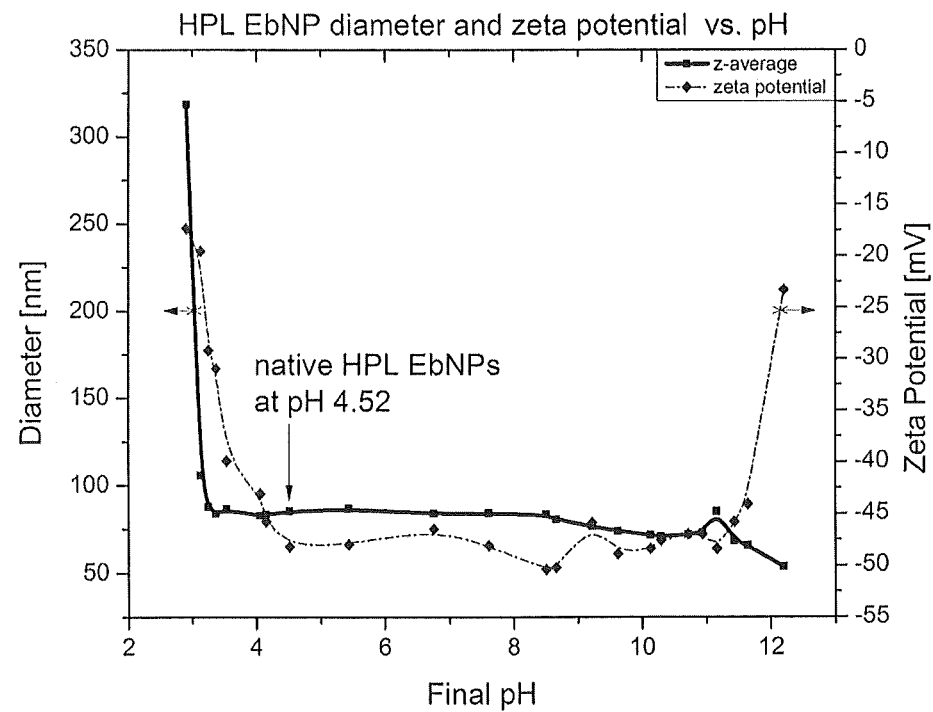
FIG. 5: HPL EbNP size and ξ-potential as a function of final pH.

The stability of HPL EbNPs against pH change was tested in dialyzed 0.10 wt % HPL EbNP samples, which were diluted down to 0.05 wt %. To adjust the pH of the EbNP suspensions, callibrated amounts of $HNO_3$ or NaOH solution were added. As indicated in FIG. 5, the pH stability of the EbNPs ranges from 3.25 to 10. Below a pH value of 3.25, the EbNPs show signs of instability and eventually aggregate as indicated with the threefold size increase at pH 2.91, which is accompanied with an apparent ξ-potential drop. When investigating the samples above pH 10, we observed a color change accompanied with reduced light scattering intensity, which was confirmed by a vanishing count rate at the DLS, indicating dissolution of HPL EbNPs.

1.2 Synthesis and Characterization of IAT EbNPs

Figure 6:
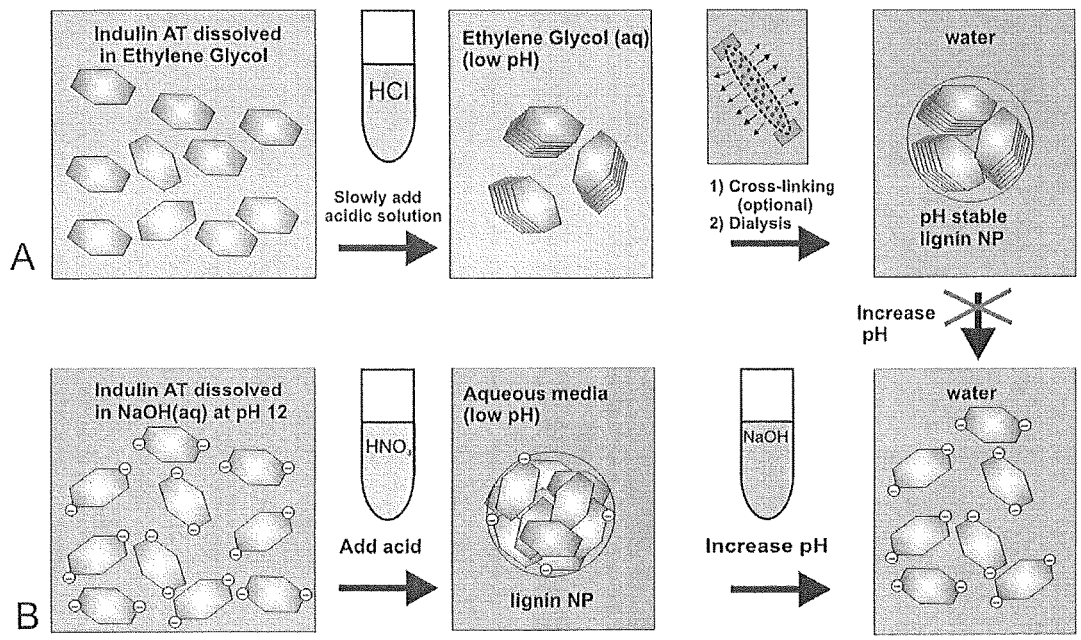
FIG. 6: Schematics of the IAT EbNP synthesis methods.[10]
Figure 7:
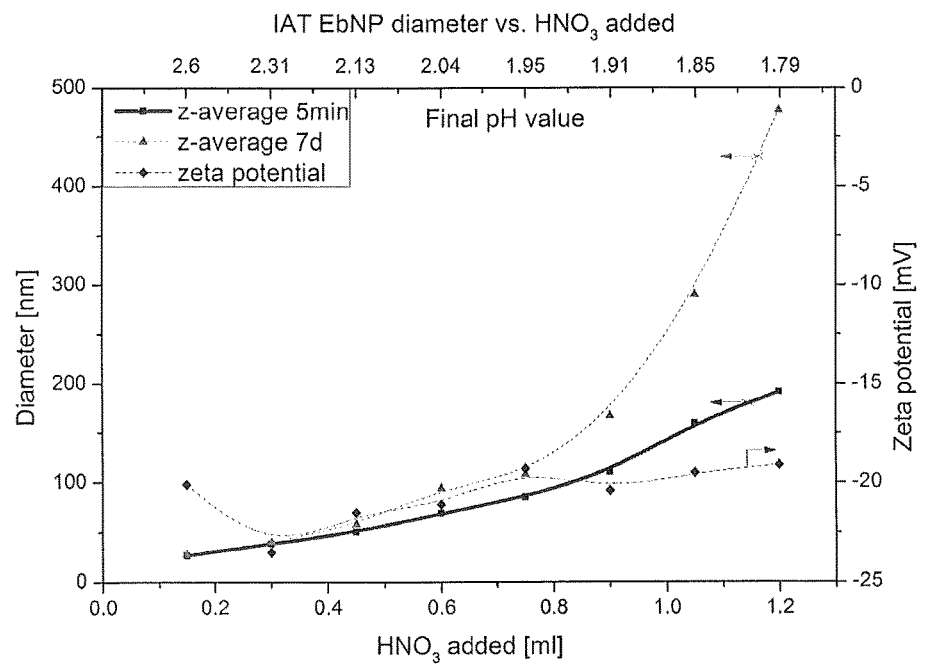
FIG. 7: Results of IAT EbNP synthesis via pH drop as a function of acid added.

FIG. 6 illustrates two IAT EbNP synthesis protocols. IAT EbNPs synthesized in ethylene glycol exhibit pH stability due to favourable stacking of the IAT molecules, while IAT EbNPs synthesized via the water-based pH drop method dissolve upon pH increase. FIG. 7 shows the diameters of IAT EbNPs synthesized via the water-based pH-drop method as a function of acid added to the system. Here, we added rapidly under vigorous stirring defined amounts of $HNO_3$ to 10 ml of 0.05 wt % IAT solution at pH 12 inducing a sudden pH drop, which triggered IAT precipitation as EbNPs. The final pH values of the samples are reported on the top x-axis. Size control could be achieved by appropriately adjusting the amount of acid added.

Figure 8:
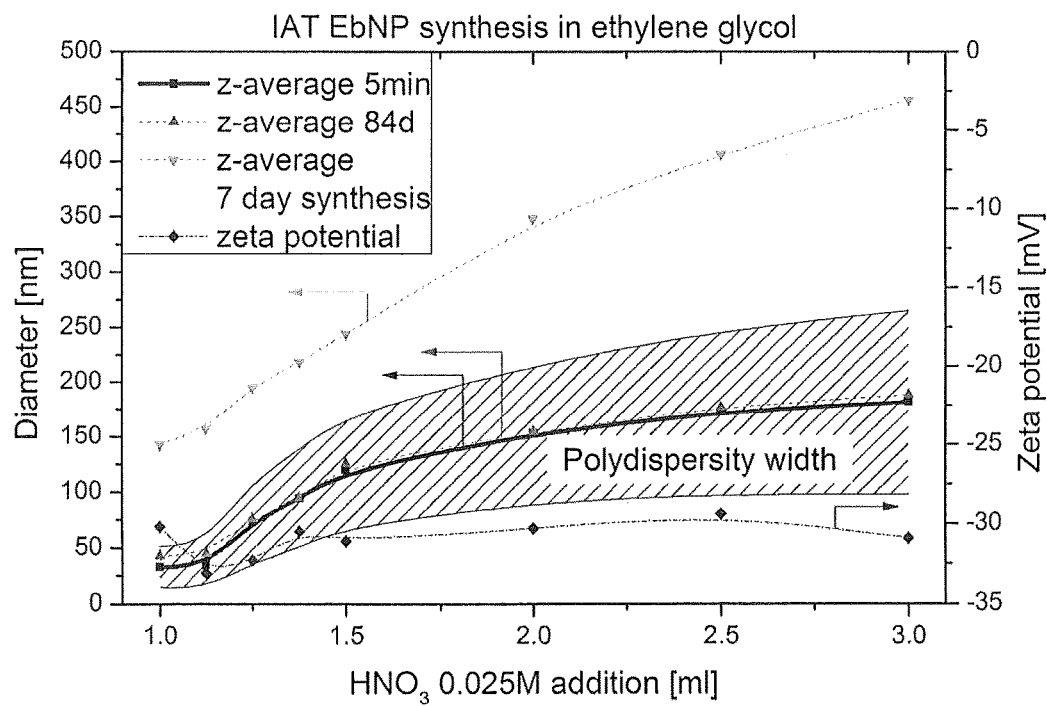
FIG. 8: IAT EbNPs size and ξ-potential vs. amount of $HNO_3$ added to 5 ml IAT0.5 wt % in ethylene glycol.

Native IAT EbNPs were synthesized via the organic solvent water-based pH-drop method in ethylene glycol and the data are reported in FIG. 8. This method allows the synthesis of IAT EbNPs with good size control in the range of 50 to 125 nm. First, 0.25 g commercial IAT lignin was dissolved in 50 ml of ethylene glycol, vortexed for 30 minutes, and filtered with a 0.45 μm syringe filter. Then, 5 ml of the stock solution was put into a 20 ml scintillation vial and vigorously stirred with a fitting magnetic stir bar. Supersaturation was induced upon addition of various amounts of acid precipitating out negatively charged IAT EbNPs. We diluted the EbNP suspension in ethylene glycol with Millipore $H_2O$, after 5 minutes and 7 days, to obtain a 0.05 wt % IAT EbNP sample, containing 10% (v/v) of ethylene glycol. The pH values measured for these final suspensions range from 3 to 4. The EbNPs exhibited a negative ξ-potential with a magnitude of approximately −30 mV for all samples. The polydispersity widths increase slightly with increasing particle diameters. The 7 day synthesis shows that the particles are growing when kept in ethylene glycol solution. The IAT EbNPs dispersed in water are stable for periods longer than 84 days.

1.2.1 IAT EbNP pH Stability

Figure 9:
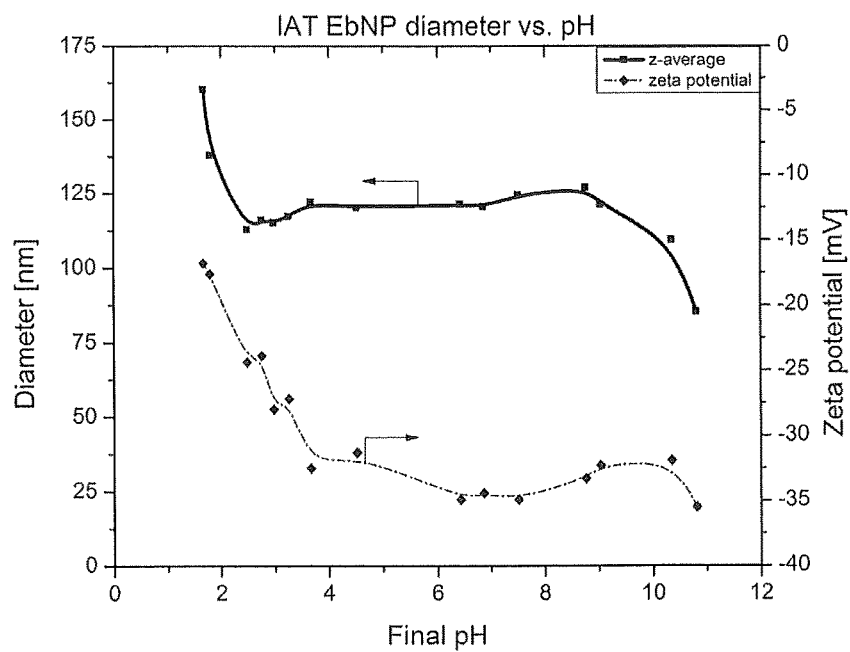
FIG. 9: IAT EbNP size and ξ-potential vs. pH.
Figure 10:
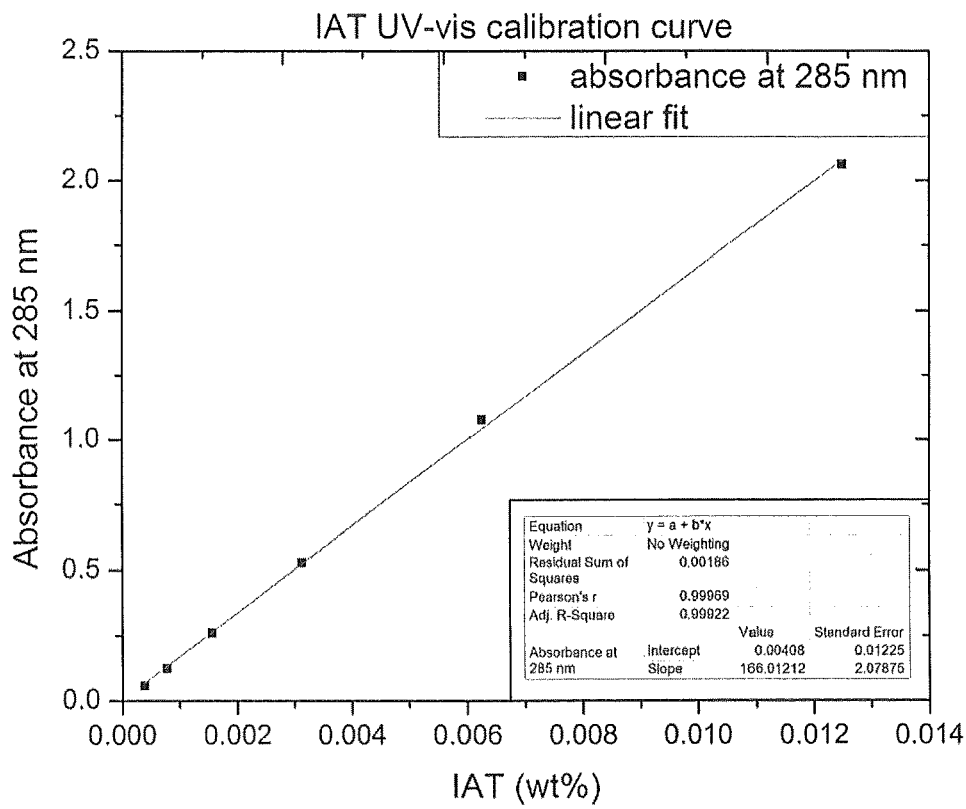
FIG. 10: IAT UV-Vis calibration curve for UV-Vis IAT EbNP solvation measurement.
Figure 11:
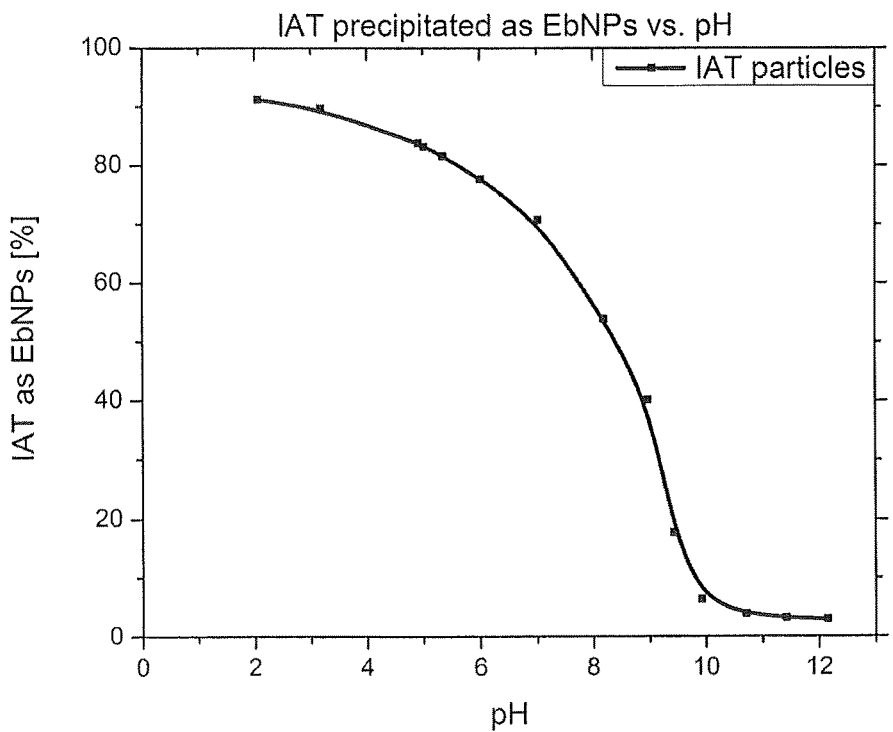
FIG. 11: IAT EbNP dissolution as a function of pH, obtained by UV-Vis measurements.

As reported in FIG. 9, the IAT EbNPs obtained are pH-stable in the pH range from 3 to 9. Here, we took dialyzed native IAT EbNP suspensions at pH 4.5 and adjusted the pH with NaOH or $HNO_3$ solution. The z-average diameter and the ξ-potential of each sample were measured. The colloidal instability of the IAT EbNP suspensions below pH 3 can be explained with the drop in ξ-potential indicating decreased electrostatic repulsion between the particles. At higher pH values, the decrease in particle size may indicate dissolution of particles. To quantify the dissolution of IAT EbNPs at elevated pH, we performed a UV-Vis study to determine the remaining amount of IAT lignin precipitated as particles as a function of increasing pH. FIG. 10 shows the UV-Vis calibration curve obtained at a wavelength of 285 nm. We utilized the curve to characterize the pH stability of IAT EbNPs as reported in FIG. 11. We started with dialyzed IAT EbNPs at pH 4.92 and adjusted the pH value afterwards. We then took the supernatant of these pre-treated samples and added aliquots of NaOH solution to baseline the samples. Then, we determined the IAT lignin dissolved in the supernatant and closed the IAT mass balance to obtain the mass of IAT EbNPs remaining in the suspension at each pH value. For example, when we increase the pH of the native EbNP suspension from pH 4.92 to pH 8.2, 53.8% of the initial IAT EbNPs remain in form of EbNPs, while 46.2% of the initial IAT EbNPs are dissolved.

1.2.2 IAT EbNP Ionic Strength Study and DLVO Modeling

Figure 12:
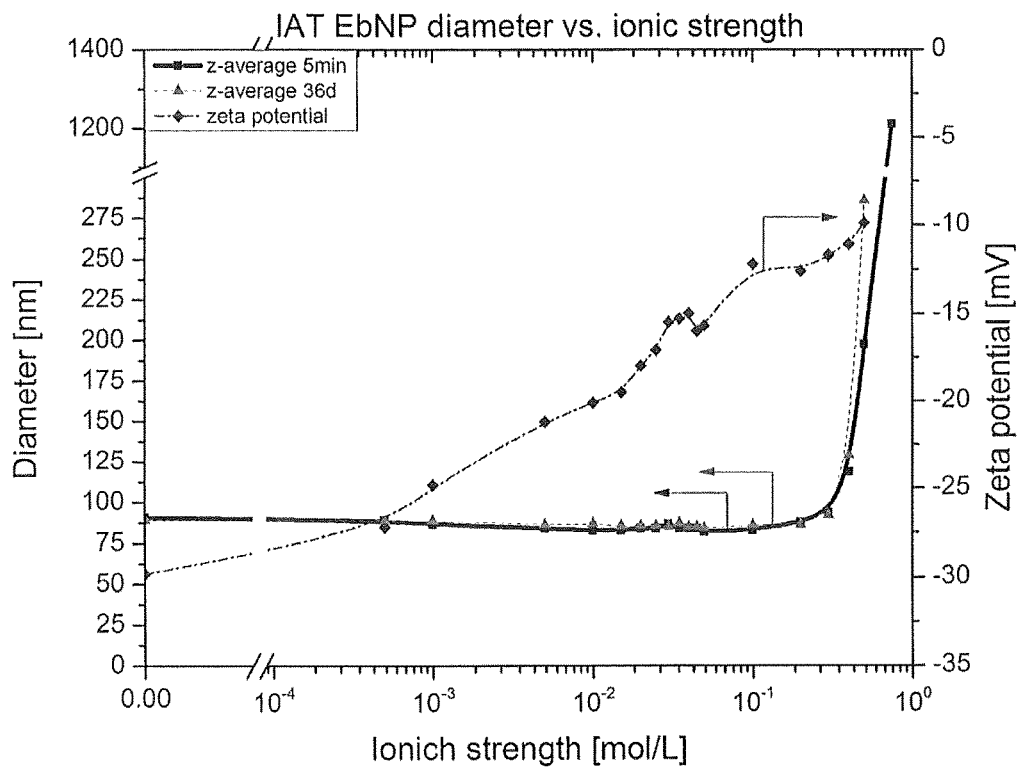
FIG. 12: IAT EbNP stability as a function of ionic strength.

We performed an ionic strength study to investigate the effect of increasing ionic strength on the stability of IAT EbNP suspensions, and to determine if the IAT EbNP suspensions may exhibit colloidal stability at ionic strength levels equivalent to the ones found in physiological testing media used in biocidal testing. FIG. 12 shows the particle diameter and ξ-potential as a function of ionic strength in mol/L. We added measured amounts of NaCl to adjust to the target ionic strength −0.10 M NaCl is equivalent to 0.10 mol/L ionic strength. The colloidal stability of the EbNP suspension was confirmed by DLS size measurements. The magnitude of the measured ξ-potential decreases rapidly upon a small increase of ionic strength. We observed that the sample at 0.30 mol/L, at an ionic strength well above the one found in physiological testing media (0.015 mol/L), exhibited colloidal stability even after 36 days. The EbNP suspensions above 0.30 M NaCl started to show signs of colloidal instability in the form of settling and aggregation.

Figure 13:
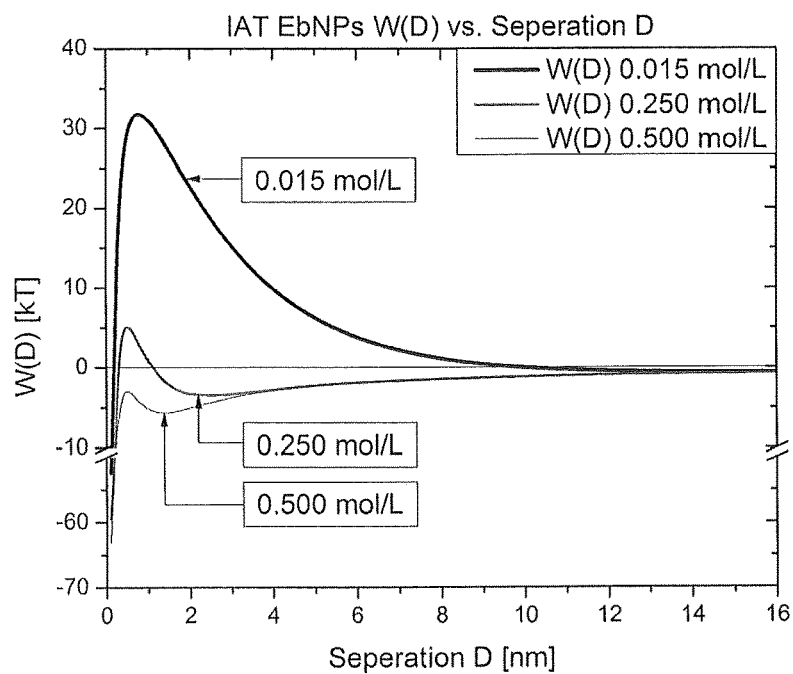
FIG. 13: DLVO modeling of IAT EbNP system. The interaction energy in kT is modeled as a function of particle separation distance in nm for three different ionic strengths.

We modeled the interaction energy W(D) according to DLVO theory in selected IAT EbNPs at three chosen ionic strengths. At an ionic strength of 0.25 mol/L, we determined a Debye length $k^{-1}$/=0.61 nm. With ξ-potential of −15.0 mV at that ionic strength, we calculated a surface potential $\Psi_0$=−40.8 mV. We determined the electrostatic repulsion energy $W(D_{elec})$ and the van der Walls attraction energy $W(D_{VDW})$ as a function of the separation distance D to evaluate the total interaction energy W(D). As shown in FIG. 13, the stability threshold in the colloidal system was determined to be at 0.25 mol/L ionic strength. The colloidal suspension at 0.50 mol/L ionic strength shows a highly unstable sample.

1.3 Characterization $Ag^+$ Ion Infused EbNPs

Figure 14:
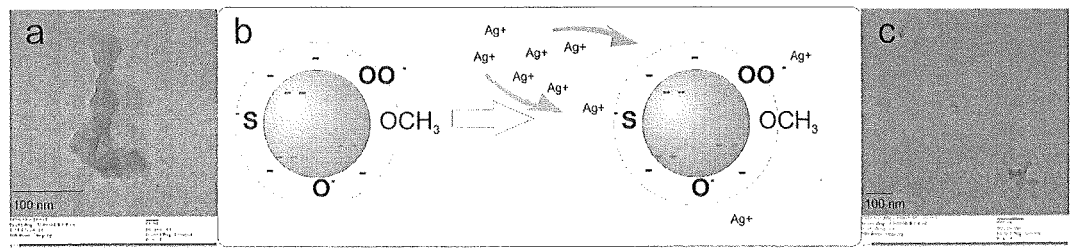
FIG. 14: Infusion of native IAT EbNPs. a, TEM micrograph of native IAT EbNP. b, Schematics showing native IAT EbNP infusion with $Ag^+$ in aqueous solution. c, TEM image of silver-ion infused IAT EbNP.

We obtained IAT EbNPs with a hydrodynamic diameter of 72 nm with a polydispersity index of 0.230 and ξ-potential of −23.5 mV. The DLS equipment measured a conductivity of 0.139 mS/cm, and an electrophoretic mobility of −1.403 μm cm/V s. As depicted in FIG. 14, TEM micrographs show predominantly nanosized non-spherical clusters in the size range below 100 nm. Some degree of spreading of IAT particles on the TEM grid could be triggered by the hydrophilic nature of IAT. The structures of the clusters suggest a high availability of surface area for particle functionalization.

We functionalized negatively charged IAT EbNPs with $Ag^+$ ions in aqueous solution. We chose a common soluble salt, $AgNO_3$, as an $Ag^+$ ion source. FIG. 14 illustrates the possible adsorption of $Ag^+$ ions on the deprotonated ionized groups on the EbNP surface. The main functional groups of IAT lignin include phenolic —OH, aliphatic —OH, carboxyl groups —OOH, and thiol groups —SH, which when deprotonated render the surface charge of TAT EbNPs negative; hence, deprotonated functional groups serve as suitable binding sites for cations including $Ag^+$ ions. The distribution of the functional groups and the respective pKa values are reported in Table 6. TEM micrographs of functionalized IAT EbNPs show predominantly nanosized non-spherical clusters in the size range below 100 nm.

Figure 15:
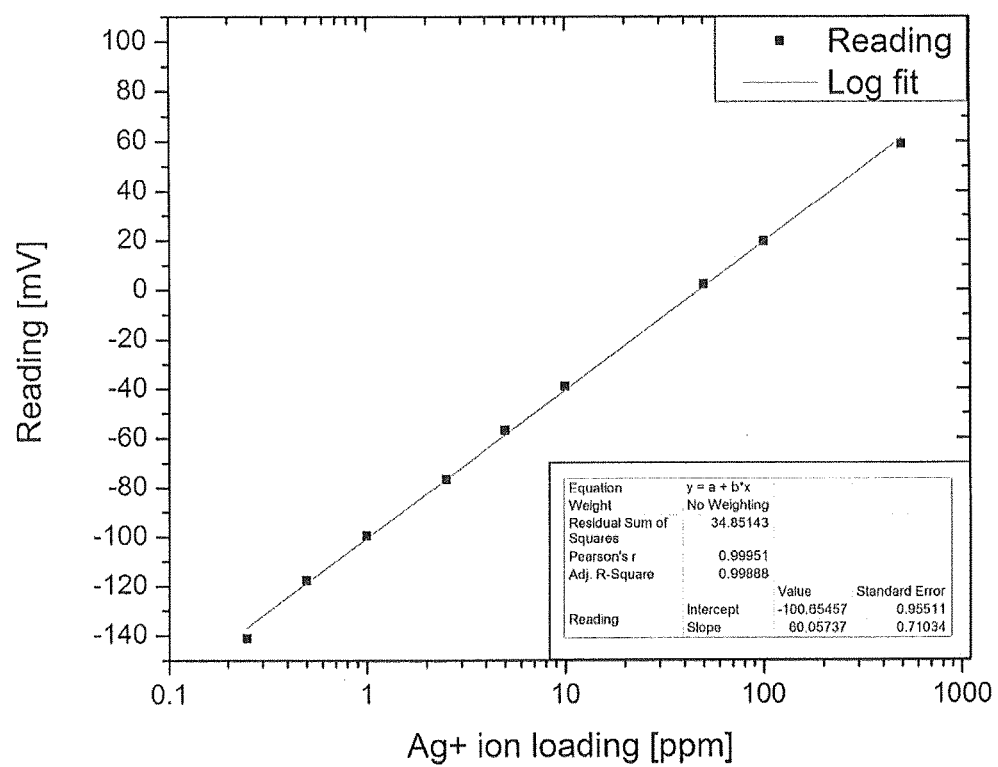
FIG. 15: $Ag^+$ calibration curve. Silver ion mV reading vs. $Ag^+$ ppm loading.

$Ag^+$ reference solutions in the range of 0.25 ppm to 500 ppm were prepared from 1000 ppm $Ag^+$ standard, and the corresponding potential in mV was recorded using an $Ag^+$ ion selective electrode in conjunction with a multimeter. Each reading was obtained after 2.5 minutes of equilibrium time. FIG. 15 shows the $Ag^+$ ion calibration curve with logarithmic fit.

We prepared additional $AgNO_3$ standards with 40 ppm $Ag^+$, 100 ppm $Ag^+$, 200 ppm $Ag^+$, and 800 ppm $Ag^+$, and added 0.5 ml of each of these standards to 9.5 ml of previously prepared 0.0526 wt % IAT EbNP suspensions to infuse the particles with $Ag^+$ ions. To determine the $Ag^+$ ion content adsorbed on the EbNPs, we first determined the residual $Ag^+$ ions in the supernatant in each sample, and then closed the $Ag^+$ ion balance to estimate the amount of $Ag^+$ ions adsorbed on the particles. The ion content in the supernatant was determined with an $Ag^+$ ion selective electrode (ISE).

Table 1 summarizes the $Ag^+$ ion infused samples with various amounts of $Ag^+$ ion loadings. The initial loading corresponds to the overall $Ag^+$ ion content in the 10 ml sample at the time of infusion. The Ag⁺ ion content in the supernatant was calculated from the mV reading at the ISE with the following equation.

$$Ag^+_{snat}[ppm] = e^{\left(\frac{ISE[mV]+100.74}{26.105}\right)}$$

We measured a negative-potential for the Ag⁺ infused IAT EbNPs.

TABLE 1

Ag⁺ adsorbtion data on particles.

| EbNP wt %, initial Ag⁺ ppm loading | Ag⁺ ion ISE [mv] | Supernatant [ppm Ag⁺] | Adsorbed on particles [ppm Ag⁺] | Ag⁺ ion adsorbed on particles [%] |
|---|---|---|---|---|
| IAT 0.05, 2 ppm | −98.80 | 0.91 | 1.09 | 54.7 |
| IAT 0.05, 5 ppm | −64.80 | 3.58 | 1.42 | 28.4 |
| IAT 0.05, 10 ppm | −44.30 | 7.70 | 2.30 | 23.0 |
| IAT 0.05, 40 ppm | −5.70 | 35.07 | 4.93 | 12.3 |

We modeled the Ag⁺ ion adsorption equilibria with a Langmuir adsorption isotherm and normalized the Ag⁺ uptake capabilities per surface area. The Langmuir adsorption isotherm is described by the following equation:

$$\Gamma(c) = \Gamma_{max}\frac{Kc}{1+Kc}$$

Figure 16:
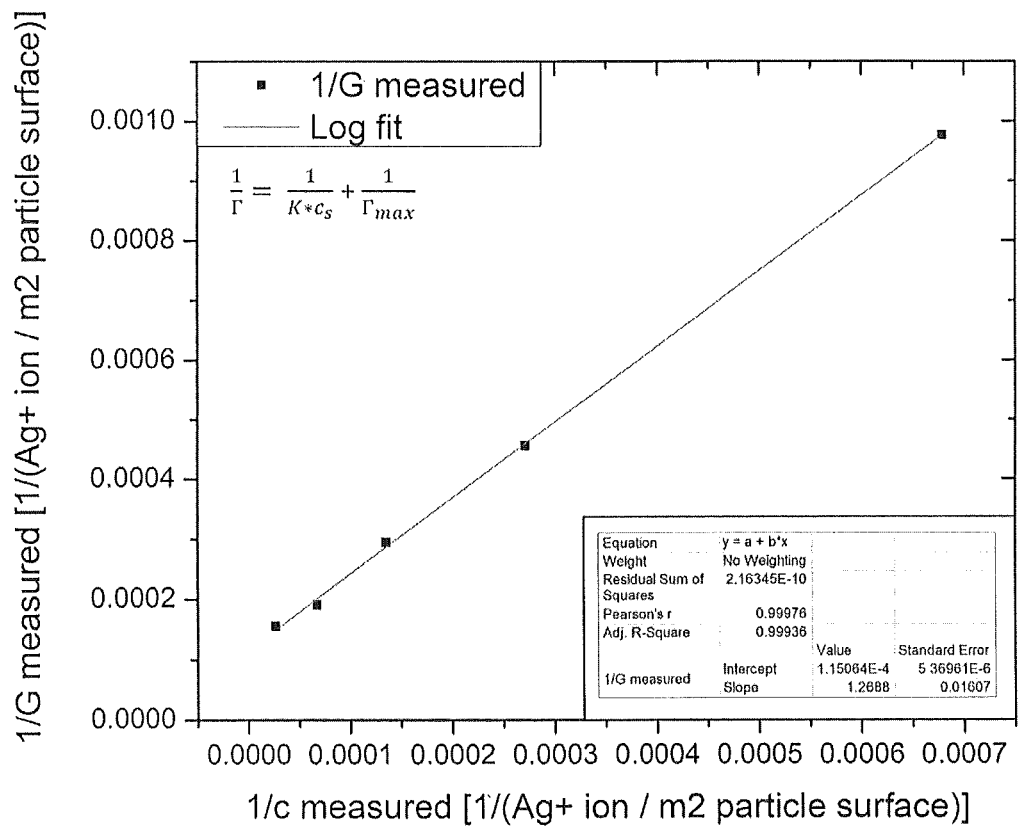
FIG. 16: Determination of $\Gamma_{max}$ and k for Langmuir adsorption isotherm.
Figure 17:
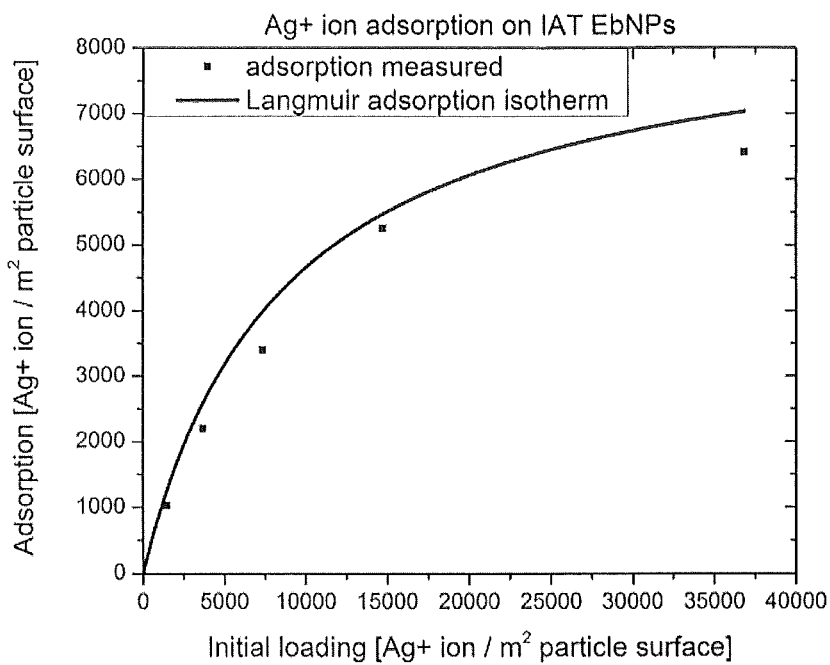
FIG. 17: Langmuir adsorption isotherm fit. $Ag^+$ adsorption on IAT EbNP nanoparticles normalized on $m^2$ particle surface area vs. initial $Ag^+$ loading per $m^2$ particle surface area.

We determined a maximal adsorption $\Gamma_{max}$=8688 ppm Ag⁺/m² particle surface area, and a K value of 0.000115 in FIG. 16. We used these parameters to model the adsorption isotherm that we report in FIG. 17. We observed that the Ag⁺ ion loading increases with an increasing amount of Ag⁺ available. The Ag⁺ absorption reaches equilibrium within 24 h. We observed that the Ag⁺ content in the supernatant stays constant after 24 h (re-measured after 3 days). We infer that the Ag⁺ is predominately physically adsorbed on the IAT binding sites.

1.4 Synthesis and Characterization of Ag-EbNPs-PDADMAC

Figure 18:
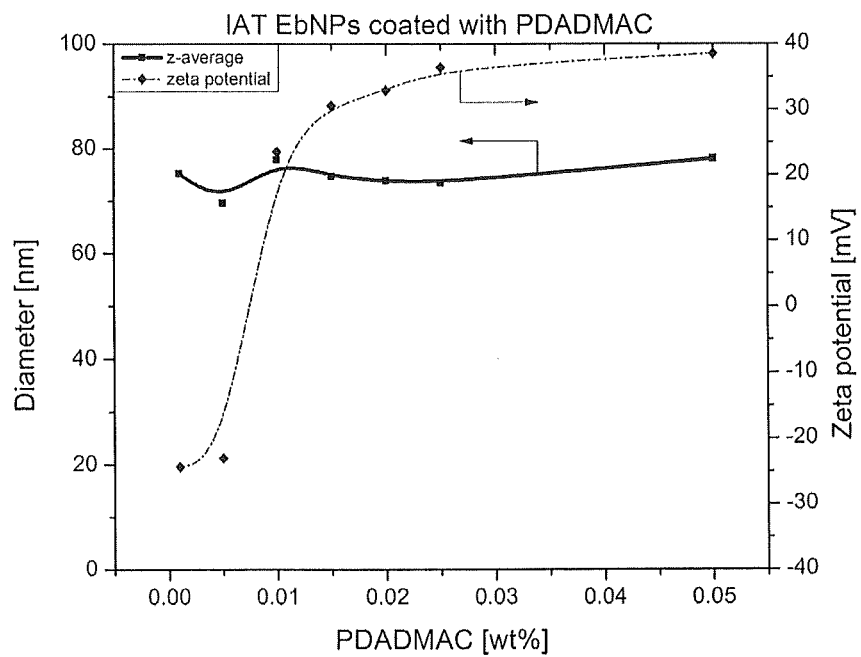
FIG. 18: EbNP diameter and ξ-potential vs, initial PDADMAC wt %.
Figure 19:
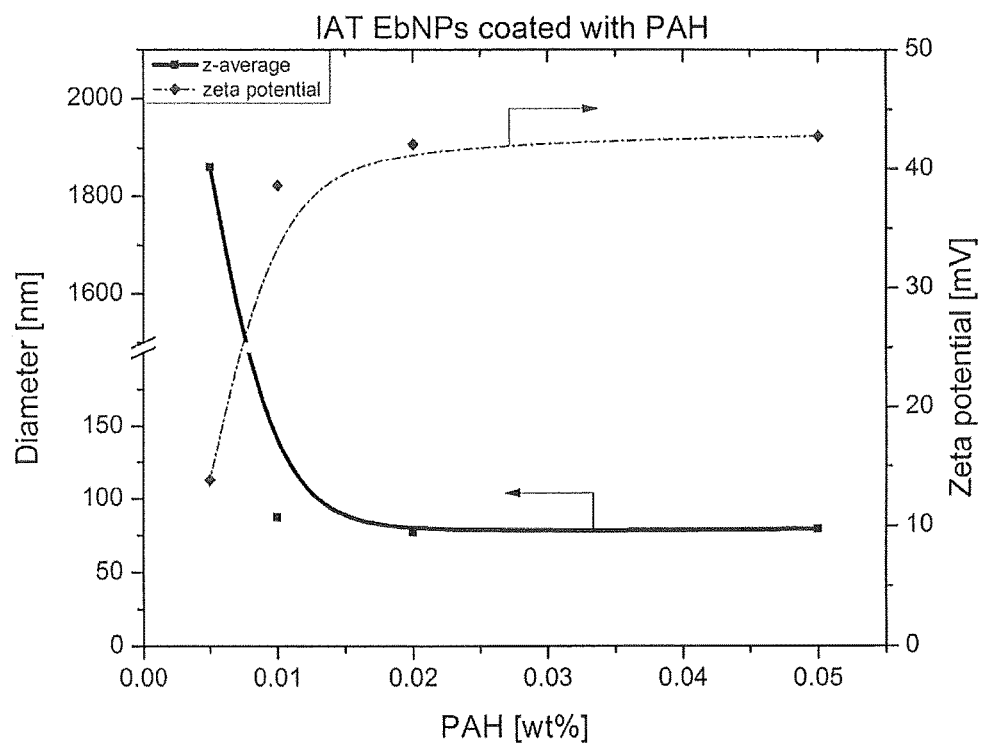
FIG. 19: EbNP diameter and ξ-potential vs. initial PAH wt %.

To allow electrostatic attraction between negatively charged bacteria in aqueous solution and the Ag⁺ ion functionalized EbNPs, we reversed the surface charge of Ag⁺ infused EbNPs from negative to positive. We modified the surface properties of the EbNP system through adsorption of PDADMAC, a positively charged polyelectrolyte. To find a suitable PDADMAC concentration for the EbNP surface modification, we prepared samples with the initial PDADMAC concentrations reported in Table 2. The particles were coated in 5 ml batches of IAT EbNP 0.05 wt % suspension. For the surface modification step, 5 ml of polyelectrolyte solution with the previously reported wt % was added rapidly to the IAT EbNP suspension. The final concentration of IAT in the sample was 0.025 wt %. To investigate the stability and the change of properties of the coated samples, we measured the z-averages and the ξ-potential with DLS. FIG. 18 illustrated the EbNP diameter and potential trends as a function of initial PDADMAC concentration. The results indicate that below addition of 0.10 wt % PDADMAC solution, the IAT EbNP surface potential does not reverse from negative to positive. At 0.15 wt % or higher, enough PDADMAC is available to reverse the surface charge to positive.

TABLE 2

Initial PDADMAC wt % and resulting ζ-potential after polyelectrolyte coating.

| PDADMAC wt % initial | dispersant) with 5% EG [nm] | ζ-potential [mV] | Comments |
|---|---|---|---|
| 0.050 | 78.07 | 38.5 | Stable |
| 0.025 | 73.4 | 36.4 | Stable |
| 0.020 | 73.81 | 32.9 | Stable |
| 0.015 | 74.65 | 30.6 | Stable |
| 0.010 | 77.86 | 23.5 | |
| 0.005 | 69.54 | −23.0 | |
| 0.001 | 75.2 | −24.3 | |

The magnitude of the positive surface potential, obtained after coating the IAT EbNPs, is dependent on the polyelectrolyte used. Similarly to the samples with PDADMAC coating reported previously, polyallylamine hydrochloride (PAH) coated IAT EbNPs were synthesized to prove the possibility to customize the surface charge magnitude by choice of suitable polyelectrolytes. The z-averages and ξ-potentials were measured and are reported in Table 3. The corresponding trends are illustrated in FIG. 18.

TABLE 3

Initial PAH wt % and resulting ζ-potential after polyelectrolyte coating.

| PAH wt % initial | z-average (adjusted dispersant) with 5% EG [nm] | zeta potential [mV] | Comments |
|---|---|---|---|
| 0.050 | 79.21 | 42.8 | stable |
| 0.020 | 76.97 | 42.1 | stable |
| 0.010 | 86.94 | 38.6 | stable |
| 0.005 | 18.59 | 13.8 | unstable |

A suitable sample obtained was Ag-EbNPs-PDADMAC (d=72 nm) with a final IAT EbNP concentration of 0.025 wt %, an Ag⁺ ion content on the particles of 0.71 ppm, an Ag⁺ ion amount in the supernatant of 1.79 ppm, and a PDADMAC concentration of 0.01 wt % in the colloidal suspension. The surface potential was reversed from −25.0 mV to +32.4 mV with the addition of PDADMAC −0.01 wt % in the final sample. The final sample pH was 5.5. Other samples were prepared accordingly.

1.5 Antimicrobial Testing

We compared the antimicrobial activity of Ag-EbNPs-PDADMAC with that of positively charged branched polyethylene imine AgNPs (BPEI AgNPs) and AgNO₃ solutions (see supplemental information for BPEI AgNP and AgNO₃ sample preparations). We performed quantitative antimicrobial tests on Gram-negative *E. coli* BL21 (DE3), a common human pathogen, and qualitative tests on Gram-negative *P. aeruginosa*, a human pathogen not susceptible to antimicrobial amines such as BPEI and PDADMAC. Therefore, any antimicrobial activity in the *P. aeruginosa* tests will predominantly stem from silver.

Figure 20:
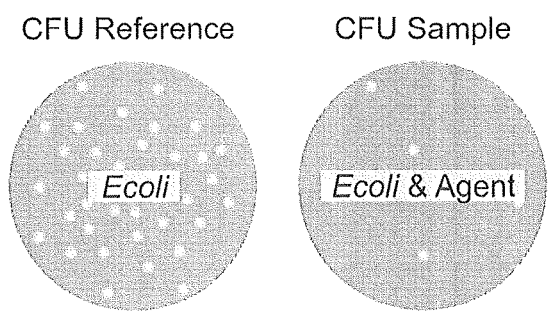
FIG. 20: CFU on reference plate without agent (left) and CFU on test plate with antimicrobial agent (right).

The activity of each active agent was determined by comparing the number of colony forming units (CFU) of a reference plate with the CFU of a test plate as depicted in FIG. 20. The reduction of CFU on a test plate with antimicrobial agent is time dependent and concentration dependent.

The maximum antimicrobial reduction efficiency of 100% was reached when no CFU could be determined on the test plate. We quantified by the antimicrobial reduction efficiency "E" with the following equation $$E = 100\left(1 - \frac{CFU\ \text{sample}}{CFU\ \text{reference}}\right)$$

Figure 21:
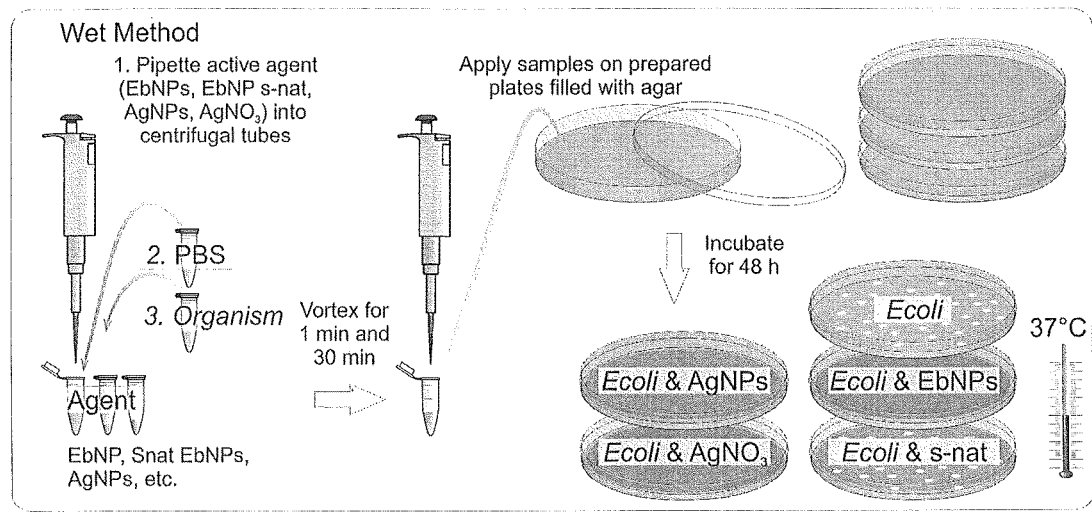
FIG. 21: Wet method schematic for antimicrobial testing. (1) placement of active agent into centrifugal tubes, (2) addition of PBS buffer, (3) addition of bacteria solution, vortexing for 1 minute and 30 minutes, platting after 1 minute and 30 minutes, incubation of samples, and investigation of CFUs.
Figure 22:
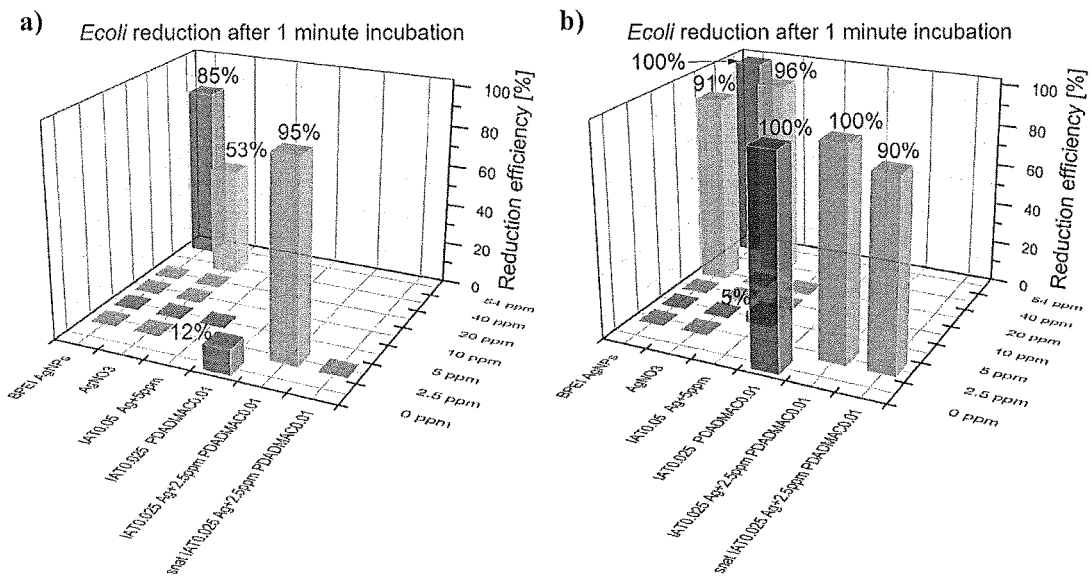
FIG. 22: Qualitative *E. coli* test—CFU reduction efficiency of selected IAT EbNP, BPEI AgNP, and $AgNO_3$ samples. a, after 1 minute incubation time. b, after 30 minutes incubation time.

The schematic in FIG. 21 describes the wet method procedure that was followed for antimicrobial tests on both *E. coli* and *P. aeruginosa*. First, 200 μl of each active agent was placed into separate low retention centrifuge tubes. 100 μl of PBS buffer was added to each tube to baseline the ionic strength, and to adjust the pH value to 7. Finally, 100 μl of bacteria, *E. coli* or *P. aeruginosa* solution with approximately 4400 CFU/ml in nutrient broth, was added. The samples were continuously vortexed. After the bacteria were exposed to the active agent for 1 minute, the survival rate of the bacteria was determined by plating 100 μl of each sample evenly distributed on Luria-Bertani agar plates. The procedure was repeated after 30 minutes of exposure time. After the plating procedure, the petri dishes were sealed and incubated upside-down for 48 h at 37° C.

1.5.1 Quantitative Antimicrobial Test on *E. Coli*

FIG. 22 and

Table 4 compare the quantitative antimicrobial efficiency of each active agent in the *E. coli* tests. The reduction efficiency of six different samples with increasing Ag ppm equivalent ranging from 0 ppm to 54 ppm was investigated. The graphs show the reduction efficiency at two time points, 1 minute and 30 minutes. The weight percentages of the control samples and the silver contents in the active agents were chosen to show antimicrobial thresholds and to facilitate comparisons between the samples. Native IAT EbNPs without Ag⁺ functionalization and surface modification did not result in any observable reduction in CFU (not reported), which suggests that the native IAT EbNPs are benign. Also, IAT EbNPs with Ag⁺ functionalization but without PDADMAC coating did not result in significant reduction of CFU after 1 minute (0%) and 30 minutes (5%). We suggest that the low antimicrobial efficiency may be attributed to the negative surface charge of these EbNPs, which may hinder them from overcoming the electrostatic barrier between the particles and the bacteria. IAT EbNPs coated with PDADMAC resulted in strong reduction of CFU after an exposure time of 30 minutes, which may be attributed to the antimicrobial effect of the quarterly amine PDADMAC. PDADMAC solution alone (not reported) exhibited strong bactericidal effects towards *E. coli* as well, comparable to the efficiency of Ag-EbNPs-PDADMAC or 100% after 30 minutes exposure time. Ag-EbNPs-PDADMAC exhibited strong reduction in CFU, prevalent after 1 minute exposure time. The corresponding supernatant of Ag-EbNPs-PDADMAC exhibited no observable effect after 1 minute. The reduction of CFU in the supernatant after 30 minutes exposure time may be explained by residue active agent in the solution. BPEI AgNPs and AgNO₃ solutions exhibited antimicrobial effects at 20 ppm Ag and 40 ppm Ag respectively. Overall, the Ag-EbNPs-PDADMAC sample outperformed the BPEI AgNPs and AgNO₃ samples in terms of antimicrobial efficiency normalized on Ag ppm equivalent.

TABLE 4

Results of quantitative *E. coli* tests. The CFU reduction efficiency of selected IAT EbNP samples, BPEI AgNP samples, and AgNO₃ samples are shown.

| Quantitative *E. coli* test; IAT EbNP samples | | | | |
|---|---|---|---|---|
| | IAT0.05 Ag⁺ 5 ppm | IAT0.025 Ag⁺ 2.5 ppm PDADMAC 0.01 | IAT0.025 PDADMAC 0.01 | snat IAT0.025 Ag⁺ 2.5 ppm PDADMAC 0.01 |
| 1 min vortex time | | | | |
| CFU reduction efficiency 30 min vortex time | no observable effect | 95.24% | 12.38% | no observable effect |
| CFU reduction efficiency | 4.76% | 100.00% | 100.00% | 89.52% |

| Quantitative *E. coli* test; AgNPs | | | | |
|---|---|---|---|---|
| BPEI AgNPs 54 ppm | BPEI AgNPs 20 ppm | BPEI AgNPs 10 ppm | BPEI AgNPs 5 ppm | BPEI AgNPs 2.5 ppm |
| 1 min vortex time | | | | |
| CFU reduction efficiency 30 min vortex time: 84.76% | no observable effect | no observable effect | no observable effect | no observable effect |
| CFU reduction efficiency: 100.00% | 91.43% | no observable effect | no observable effect | no observable effect |

| Quantitative *E. coli* test; AgNO3 | | | | |
|---|---|---|---|---|
| AgNO3 40 ppm | AgNO3 20 ppm | AgNO3 10 ppm | AgNO3 5 ppm | AgNO3 2.5 ppm |

TABLE 4-continued

Results of quantitative *E. coli* tests. The CFU
reduction efficiency of selected IAT EbNP samples, BPEI
AgNP samples, and AgNO₃ samples are shown.

| 1 min vortex time | | | | | |
|---|---|---|---|---|---|
| CFU reduction efficiency | 53.33% | no observable effect | no observable effect | no observable effect | no observable effect |

TABLE 4-continued

Results of quantitative *E. coli* tests. The CFU
reduction efficiency of selected IAT EbNP samples, BPEI
AgNP samples, and AgNO₃ samples are shown.

| 30 min vortex time | | | | | |
|---|---|---|---|---|---|
| CFU reduction efficiency | 96.19% | no observable effect | no observable effect | no observable effect | no observable effect |

1.5.2 Qualitative Antimicrobial Test on *P. Aeruginosa*

Figure 23:
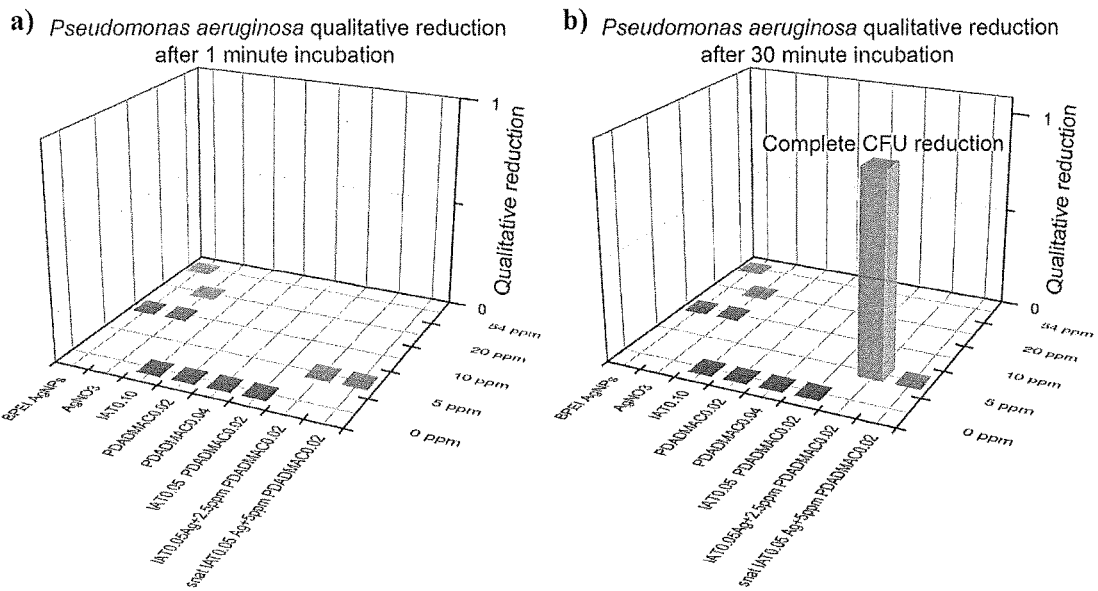
FIG. 23: Quantitative *Pseudomonas aeruginosa* test—CFU reduction efficiency of selected BPEI AgNP, $AgNO_3$, PDADMAC, and IAT EbNP samples. a, after 1 minute incubation time. b, after 30 minutes incubation time.
Figure 24:
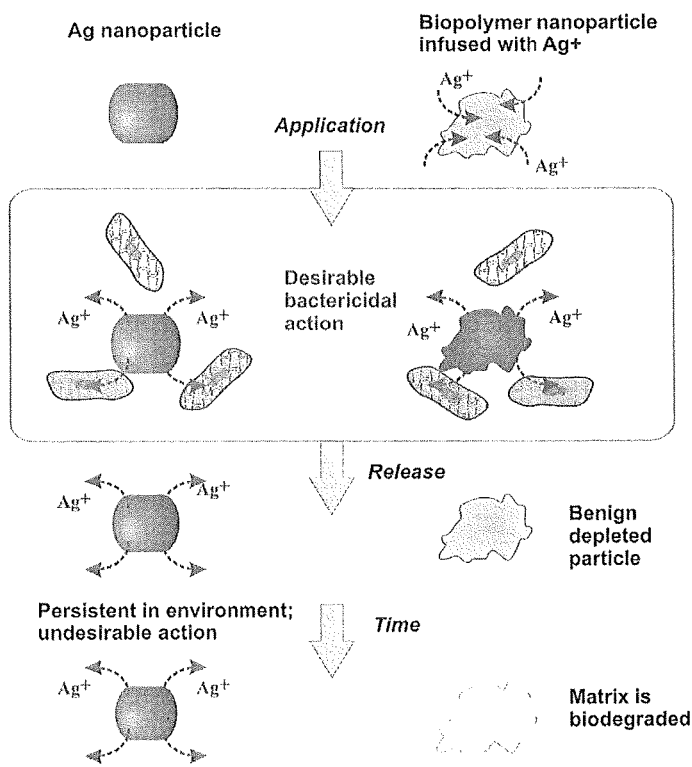
FIG. 24: Schematics of the concept for making and using environmentally benign bactericidal nanoparticles (EbNPs) compared to the present use of AgNPs.

As mentioned previously, the qualitative antimicrobial test on *P. aeruginosa* can distinguish the antimicrobial effect of PDADMAC from the effect of silver. FIG. 23 and Table 5 compare the qualitative antimicrobial efficiency of each active agent in this test. BPEI AgNPs and AgNO₃ solutions exhibited no complete antimicrobial effect after 30 minutes incubation time at 54 ppm Ag and 20 ppm Ag respectively. The control sample IAT EbNP at an elevated wt % of 0.10 did not result in any observable effect. Also, the sample IAT EbNPs coated with PDADMAC did not exhibit any measurable antimicrobial effect. The PDADMAC solutions at 0.02 wt % and 0.04 wt % appeared to promote *P. aeruginosa* growth. The sample Ag-EbNPs-PDADMAC was the only one that exhibited complete or 100% antimicrobial efficiency after 30 minutes. The supernatant of the sample Ag-EbNPs-PDADMAC did not show any antimicrobial effect after 30 minutes of incubation time. As the control samples of PDADMAC 0.02 wt %, PDADMAC 0.04 wt %, and the IAT EbNP sample coated with PDADMAC were ineffective in terms of complete antimicrobial efficiency after 30 minutes of incubation time, the results suggest that the antimicrobial action of Ag-EbNPs-PDADMAC is delivered by silver ions. Comparing all active agents tested in terms of antimicrobial efficiency, we establish that Ag-EbNPs-PDADMAC proved most effective.

TABLE 5

Result table of qualitative *Pseudomonas aeruginosa* test. Each picture corresponds to the four reported CFU tests in the table above. After 30 min of vortexing, growth was observed in bacteria treated with BPEI AgNPs 54 ppm, AgNO₃ 20 ppm, PDADMAC 0.04 wt % solution, IAT EbNPs 0.10 wt %, IAT EbNPs 0.05 wt % coated with PDADMAC 0.02 wt %, and the supernatant of 0.05 wt % Ag-EbNPs-PDADMAC. The active agent 0.05 wt % Ag-EbNPs-PDADMAC was the only active agent resulting in no growth or 100% reduction in CFU.

Qualitative *P. aeruginosa* test

| | BPEI AgNPs 10 ppm | BPEI AgNPs 54 ppm | AgNO₃ 10 ppm | AgNO₃ 20 ppm | PDADMAC 0.02 | PDADMAC 0.04 | IAT0.10 | IAT0.05 PDADMAC 0.02 | IAT0.05 Ag⁺ 5 ppm PDADMAC 0.02 | snat IAT0.05 Ag⁺ 5 ppm PDADMAC 0.02 |
|---|---|---|---|---|---|---|---|---|---|---|
| 1 min vortex time or contact time | | | | | | | | | | |
| *Pseudomonas aeruginosa* growth | Yes | Yes | Yes | Yes | Yes | Yes | Yes | Yes | Yes | Yes |
| 30 min vortex time or contact time | | | | | | | | | | |
| *Pseudomonas aeruginosa* growth | Yes | Yes | Yes | Yes | Yes | Yes | Yes | Yes | No | Yes |

2 CONCLUSION

We developed a new class of nanomaterials with increased efficiency and potentially improved nanoparticle post-utilization safety. Functionalized environmentally benign nanoparticles (EbNPs) exhibit locally confined and temporarily limited bioactivity. Other than their persistent counterparts, they are predominately made from biodegradable and sustainable materials, and are synthesized via green chemistry. As these EbNPs may lose their activity due to depletion of agent, dissolution of the EbNP system, or degradation of the lignin-based matrix by the environment, they can minimize any potential nanomaterial waste hazards. In addition to the beneficial post-utilization performance, EbNPs may deliver higher efficiency in terms of active agent employed in comparison to persistent nanoparticle system. In biocidal tests on the human pathogens *E. coli* and *P. aeruginosa*, we proved that silver ion infused EbNPs with positive surface charge (Ag-EbNP-PDADMAC) exhibit significantly higher antimicrobial activities in terms of Ag equivalent than silver nanoparticles. The increased efficiency of EbNPs with functional equivalent to their persistent counterparts, may favor substitution of a wide range of applied metal nanoparticles. Moreover, the benign nature of f-EbNPs opens opportunities for new applications of nanoparticles in the agriculture, home and personal care, and pharmaceutical industry.

3 EXPERIMENTAL SECTION

Equipment

DLS (Malvern Instruments Ltd., Nano ZS, λ=633 nm, max. 5 mW)
Syringe pump (New Area Pump Systems, NE-4000)
UV-Vis spectrometer (Jasco UV/Vis V-550 spectrophotometer)
UV lamp (Uvitron, Sunray 400SM)
Multimeter (Mettler Toledo, S80)

Materials and Chemicals Used in EbNP Synthesis.

Lignin.

We obtained INDULIN AT lignin (IAT) powder (lot MB05) and supporting documentation from MeadWestVaco (MWV) Charleston, S.C. We estimated the distribution of the main functional groups per 100 aromatic units according to the literature provided by MWV, and assigned pKa values from tables. We obtained High Purity Lignin (HPL) powder and supporting documentation from Lignol Burnaby, BC, Canada, and assigned pKa values to its functional groups accordingly. Table 6. FIG. 6 shows the distribution of functionality of the main functional groups of both lignins.

TABLE 6

Main functional groups of IAT and HPL lignin, and their pKa values.

| Lignin functional groups | IAT, distribution of functionality (#/100 aromatic units) | HPL, distribution of functionality (#/100 aromatic units) | pKa |
|---|---|---|---|
| Phenolic OH | 68 | 73 | 10 |
| Aliphatic OH | 51 | 34 | 18 |
| SH | 9 | — | 10.75 |
| COOH | 16.02 | — | 4.2 |
| OCH3 | 82 | 114 | 10.2 |
| Carbonyl - O | 12 | — | — |
| Aryl alkyl ether | 36 | — | — |
| Dialkyl ether | 9 | — | — |

Millipore water (Synergy UV); acetone (BDH, CAS#67-64-1, lot 010612B); $HNO_3$ (Sigma Aldrich, CAS#7697-37-2, lot A0294591); ethylene glycol (Sigma Aldrich, CAS#107-21-1, grade 99+%, lot B0521395); 0.45 μm syringe filter (Thermo Scientific, nylon syringe filter 0.45 μm); magnetic stir bar (Fisher Scientific, 8-Agon stir bar 14-512-147).

HPL EbNP Synthesis.

The ξ-potential was measured with a Malvern disposable capillary cell DTS 1061. The following measuring settings were used: the solvent was $H_2O$ with 10% (v/v) acetone with an overall viscosity of 1.0684 cP. The effective voltage was 150 V.

IAT EbNP Synthesis.

The ξ-potential was measured with a Malvern disposable capillary cell DTS1061 in the size control and pH-stability studies. The following measuring settings were used: the solvent was $H_2O$ with 10% (v/v) ethylene glycol with an overall viscosity of 1.1932 cP. The effective voltage was 150 V. The ξ-potential was measured with a Malvern dip cell ZEN1002 in the ionic strength study. The dip cell allows ξ-potential analysis with low driving voltages. The following measuring settings were used: the solvent was $H_2O$. The voltage was automatically adjusted by the equipment and chosen at values below 5.0 V for all measurements.

IAT EbNP Functionalization with $Ag^+$ Ions.

$Ag^+$ standard (Mettler Toledo, silver ISE standard 1000 ppm 51344770, lot ISEAG510L1); $Ag^+$ ion selective electrode (Mettler Toledo, silver/sulfur electrode 51302822, reference filling solution C 51344752).

Reference Samples BPEI AgNPs and $AgNO_3$ Solution.

Positively charged branched polyethylene imine (BPEI, Sigma Aldrich, Mw ~25000 by LS, CAS#9002-98-6, lot MKB64206V) coated AgNPs with a z-average diameter of 20 nm were synthesized according to the literature.[29] The molar ratio of the final AgNP solution was chosen to be 0.5 mM BPEI: 0.5 mM $AgNO_3$ (Fisher Chemicals, CAS#7761-88-8, lot 016932): 0.1 mM HEPES buffer (Sigma Aldrich, CAS#7365-45-9, lot 98H5425). 10 ml of the mixture was exposed to UV light for 120 minutes to form BPEI capped AgNPs with 54 ppm silver equivalent. The z-average diameter was determined with DLS. The pH value of the final solution was 6.3. $AgNO_3$ solutions were prepared from a 1000 ppm $Ag^+$ reference standard. The target ppm concentrations for antimicrobial testing were reached by appropriately diluting the reference standard with Millipore water.

Media Used in Antimicrobial Testing.

PBS buffer (Sigma Aldrich, CAS#7778-77-0, lot 38H8503), LB ager (Fischer Chemicals, CAS#9002-18-0), LB broth (Acros 61187-5000, lot B012260G).

4. REFERENCES

Section 1

1. Bystrzejewska-Piotrowska, G.; Golimowski, J.; Urban, P. L., Nanoparticles: Their potential toxicity, waste and environmental management. *Waste Management* 2009, 29 (9), 2587-2595.
2. Stem, S. T.; McNeil, S. E., Nanotechnology Safety Concerns Revisited. *Toxicological Sciences* 2008, 101(1), 4-21.
3. Walser, T.; Limbach, L. K.; Brogioli, R.; Erismaim, E; Flamigni, L.; Hattendorf, B.; Juchli, M.; Krumeich, F.; Ludwig, C.; Prikopsky, K.; Rossier, M.; Saner, D.; Sigg, A.; Hellweg, S.; Gunther, D.; Stark, W. J., Persistence of engineered nanoparticles in a municipal solid-waste incineration plant. *Nat Nano* 2012, advance online publication.
4. Lora, S. H.; Glasser, W. G., Recent Industrial Applications of Lignin: A Sustainable Alternative to Nonrenewable Materials. *Journal of Polymers and the Environment* 2002, 10 (1), 39-48.
5. Iiyama, K.; Lam, T.; Stone, B. A., Covalent Cross-Links in the Cell Wall. *Plant Physiol.* 1994, 104 (2), 315-320.
6. Glasser, W. G.; Barnett, C. A.; Muller, P. C.; Sarkanen, K. V., The chemistry of several novel bioconversion lignins. *J Agr Food Chem* 1983, 31(5), 921-930.
7. Chakar, F. S.; Ragauskas, A. J., Review of current and future softwood kraft lignin process chemistry. *Industrial Crops and Products* 2004, 20 (2), 131-141.
8. Guo, X.; Zhang, S.; Shan, X.-q., Adsorption of metal ions on lignin. *Journal of Hazardous Materials* 2008, 151(1), 134-142.
9. Harmita, H.; Karthikeyan, K. G.; Pan, X., Copper and cadmium sorption onto kraft and organosolv lignins. *Bioresource Technology* 2009, 100 (24), 6183-6191.
10. Frangville, C.; Rutkevicius, M.; Richter, A. P.; Velev, O. D.; Stoyanov, S.; Paunov, V. N., Fabrication of Environmentally Biodegradable Lignin Nanoparticles. *ChemPhysChem* 2012, 13 ((in press)).
11. Panáček, A.; Kvítek, L.; Prucek, R.; Kolář M.; Večeřová, R.; Pizúrová, N.; Sharma, V. K.; Nevěčná, T. j.; Zbořil, R., Silver Colloid Nanoparticles: Synthesis, Characterization, and Their Antibacterial Activity. *The Journal of Physical Chemistry B* 2006, 110 (33), 16248-16253.
12. Cohen, S, N.; Chang, A. C. Y.; Hsu, L., Nonchromosomal Antibiotic Resistance in Bacteria: Genetic Transformation of *Escherichia coli* by R-Factor DNA. *Proceedings of the National Academy of Sciences* 1972, 69 (8), 2110-2114.
13. Poole, K.; Krebes, K.; McNally, C.; Neshat, S., Multiple antibiotic resistance in *Pseudomonas aeruginosa*: evidence for involvement of an efflux operon. *Journal of Bacteriology* 1993, 175 (22), 7363-7372.
14. Carmeli, Y.; Troillet, N.; Karchmer, A. W.; Samore, M. H., HEalth and economic outcomes of antibiotic resistance in *pseudomonas aeruginosa*. *Archives of Internal Medicine* 1999, 159 (10), 1127-1132.
15. Cohen, M. L., Epidemiology of Drug Resistance: Implications for a Post-Antimicrobial Era. *Science* 1992, 257 (5073), 1050-1055.
16. Samuel, U.; Guggenbichler, J. P., Prevention of catheter-related infections: the potential of a new nano-silver impregnated catheter. *Int J Antimicrob Ag* 2004, 23, Supplement 1 (0), 75-78.
17. Gosheger, G.; Hardes, J.; Ahrens, H.; Streitburger, A.; Buerger, H.; Erren, M.; Gunsel, A.; Kemper, F. H.; Winlcelmann, W.; von Eiff, C., Silver-coated megaendoprostheses in a rabbit model—an analysis of the infection rate and toxicological side effects. *Biomaterials* 2004, 25 (24), 5547-5556.
18. Ohashi, S.; Saku, S.; Yamamoto, K., Antibacterial activity of silver inorganic agent YDA filler. *Journal of Oral Rehabilitation* 2004, 31 (4), 364-367.
19. Klasen, H. J., A historical review of the use of silver in the treatment of burns. II. Renewed interest for silver. *Burns* 2000, 26 (2), 131-138.
20. Lee, H. J.; Yeo, S. Y.; Jeong, S. H., Antibacterial effect of nanosized silver colloidal solution on textile fabrics. *J Mater Sci* 2003, 38 (10), 2199-2204.
21. Jain, P.; Pradeep, T., Potential of silver nanoparticle-coated polyurethane foam as an antibacterial water filter. *Biotechnol Bioeng* 2005, 90 (1), 59-63.
22. Kulthong, K.; Srisung, S.; Boonpavanitchakul, K.; Kangwansupamonkon, W.; Maniratanachote, R., Determination of silver nanoparticle release from antibacterial fabrics into artificial sweat. *Particle and Fibre Toxicology* 2010, 7 (1), 8.
23. Paddle-Ledinek, J. E. M. S., A. M; Nasa, Zeyad B. Sc; Cleland, Heather J. F.R.A.C.S, Effect of Different Wound Dressings on Cell Viability and Proliferation. *Plastic & Reconstructive Surgery. Current Concepts in Wound Healing.* 2006, 117 (7S).
24. Arora, S.; Jain, J.; Rajwade, J. M.; Paknikar, K. M., Cellular responses induced by silver nanoparticles: In vitro studies. *Toxicology Letters* 2008, 179 (2), 93-100.
25. Arora, S.; Jain, J.; Rajwade, J. M.; Paknikar, K. M., Interactions of silver nanoparticles with primary mouse fibroblasts and liver cells. *Toxicology and Applied Pharmacology* 2009, 236 (3), 310-318.
26. Ahamed, M.; AlSalhi, M. S.; Siddiqui, M. K. J., Silver nanoparticle applications and human health. *Clinica Chimica Acta* 2010, 411 (23-24), 1841-1848.
27. Kumar, A.; Vemula, P. K.; Ajayan, P. M.; John, G., Silver-nanoparticle-embedded antimicrobial paints based on vegetable oil. *Nat Mater* 2008, 7 (3), 236-241.
28. Raveendran, P.; Fu, J.; Wallen, S. L., Completely "Green" Synthesis and Stabilization of Metal Nanoparticles. *J Am Chem Soc* 2003, 125 (46), 13940-13941.
29, Jose Ruben, M.; Jose Luis, E.; Alejandra, C.; Katherine, H.; Juan, B. K.; Jose Tapia, R.; Miguel Jose, Y., The bactericidal effect of silver nanoparticles. *Nanotechnology* 2005, 16 (10), 2346.
30. Neal, A., What can be inferred from bacterium-nanoparticle interactions about the potential consequences of environmental exposure to nanoparticles? *Ecotoxicology* 2008, 17 (5), 362-371.
31. Pal, S.; Tak, Y. K.; Song, J. M., Does the Antibacterial Activity of Silver Nanoparticles Depend on the Shape of the Nanoparticle? A Study of the Gram-Negative Bacterium *Escherichia coli*. *Applied and Environmental Microbiology* 2007, 73 (6), 1712-1720.
32. Davies, D. G.; Parsek, M. R.; Pearson, J. P.; Iglewski, B. H.; Costerton, J. W.; Greenberg, E. P., The Involvement of Cell-to-Cell Signals in the Development of a Bacterial Biofilm. *Science* 1998, 280 (5361), 295-298.
33. Kvitek, L.; Panaček, A.; Soukupova, J.; Kolar, M.; Večerova, R.; Prucek, R.; Holecova, M.; Zboril, R., Effect of Surfactants and Polymers on Stability and Antibacterial Activity of Silver Nanoparticles (NPs). *The Journal of Physical Chemistry C* 2008, 112 (15), 5825-5834.
34. Liz-Marzán, L. M.; Lado-Touriño, I., Reduction and Stabilization of Silver Nanoparticles in Ethanol by Nonionic Surfactants. *Langmuir* 1996, 12 (15), 3585-3589.
35. Klibanov, A. M., Permanently microbicidal materials coatings. *J Mater Chem* 2007, 17 (24), 2479-2482.
36. El Badawy, A. M.; Silva, R. G.; Morris, B.; Scheckel, K. G.; Suidan, M. T.; Tolaymat, T. M., Surface Charge-Dependent Toxicity of Silver Nanoparticles. *Environmental Science & Technology* 2010, 45 (1), 283-287.
37. Rai, M.; Yadav, A.; Gade, A., Silver nanoparticles as a new generation of antimicrobials. *Biotechnology Advances* 2009, 27 (1), 76-83.
38. Xiu, Z.-m.; Zhang, Q.-b.; Puppala, H. L.; Colvin, V. L.; Alvarez, P. J. J., Negligible Particle-Specific Antibacterial Activity of Silver Nanoparticles. *Nano Lett* 2012.
39. Matsumura Y., Y. K.; Kunisaki S., and Tsuchido T., Mode of Bactericidal Action of Silver Zeolite and Its Comparison with That of Silver Nitrate. *Appl. Environ. Microbiol.* 2003, 69 (7), 4278-4281.
40. Feng, Q. L.; Wu, J.; Chen, G. Q.; Cui, F. Z.; Kim, T. N.; Kim, J. O., A mechanistic study of the antibacterial effect of silver ions on *Escherichia coli* and *Staphylococcus aureus*. *Journal of Biomedical Materials Research* 2000, 52 (4), 662-668.
41, Liau, S. Y.; Read, D. C.; Pugh, W. J.; Furr, J. R.; Russell, A. D., Interaction of silver nitrate with readily identifiable groups: relationship to the antibacterialaction of silver ions. *Letters in Applied Microbiology* 1997, 25 (4), 279-283.
42. Adair, F. W.; Geftic, S. G.; Gelzer, J., Resistance of *Pseudomonas* to Quaternary Ammonium Compounds. I. Growth in Benzalkonium Chloride Solution. *Applied Microbiology* 1969, 18 (3), 299-302.
43. Langsrud, S.; Sundheim, G.; Borgmann-Strahsen, R., Intrinsic and acquired resistance to quaternary ammonium compounds in food-related *Pseudomonas* spp. *Journal of Applied Microbiology* 2003, 95 (4), 874-882.
44. Tan, S.; Erol, M.; Attygalle, A.; Du, H.; Sukhishvili, S., Synthesis of Positively Charged Silver Nanoparticles via Photoreduction of AgNO3 in Branched Polyethyleneimine/HEPES Solutions. *Langmuir* 2007, 23 (19), 9836-9843.

Section 2

As depicted in FIG. 1, in contrast to permanent nanoparticle systems exhibiting post utilization hazards for humans and the environment, due to nanoparticle migration, accumulation, and persistent activity, the object of the present invention—functionalized EbNPs—have increased nanomaterial safety as they will biodegrade after their intended use minimizing any hazardous effects stemming from nanomaterial waste. Means of synthesizing native EbNPs from biopolymers via green synthesis methods in simple, inexpensive, and non-toxic ways are illustrated. Functionalization options via adsorption of and/or infusion with active agents are described. A range of procedures to alter the EbNP pH stability, colloidal stability in water or organic media, and surface properties have been developed. Silver-infused EbNPs with positive surface charge capable of releasing antimicrobial silver ions were synthesized, and evidence for complete functional equivalency to high-volume nanoparticles currently employed in industry—antimicrobial silver nanoparticles (AgNPs)—was demonstrated. In biocidal tests on human pathogens such as *E. coli* BL21 (DE3) and *Pseudomonas aeruginosa*, the EbNPs showed higher efficiency in comparison to AgNPs, and silver nitrate ($AgNO_3$) solution. While the native EbNPs did not exhibit any observable biocidal activity, positively charged EbNPs infused with silver ions demonstrated significantly higher antimicrobial efficiency. In addition to the beneficial performance with less active agent favoring substitution of AgNPs and others with EbNPs with functional equivalency, the benign nature of the invention opens opportunities for new applications in safety sensitive applications including the food and drug industry.

The invention can be used as a platform technology for versatile synthesis of functionalized EbNPs, in achieving functionality and efficiency, in formulation, and in applications, and environmental safety and biodegradability at the same time. These EbNPs are systemized from natural materials available in abundance, potentially from waste or bio-products streams, by employing simple processes using green or no organic solvents. In addition to their safety, efficiency, and cost advantages, the benign nature of the new EbNPs opens multiple utilization opportunities in markets closed for persistent nanoparticles. The advantageous features of the invention include:

- Process novelty: The synthesis procedures for persistent nanoparticle systems often involve hazardous materials, complex methods, and reactions at elevated or reduced temperatures, but only yield small output volumes/yields. Functionalized environmentally benign nanoparticles (EbNPs) are (1) made of sustainable materials and synthesized via novel, green, simple, and scalable methods, (2) functionalized with active agent, and (3) surface modified to achieve complete functional equivalency. Large yields and unmatched cost advantage in comparison to a variety of permanent and hazardous metal or semiconductor nanoparticles can be achieved.
- Functionality and Efficiency: Nanoparticles made entirely of active agent may not make efficient use of the agent. Functionalized EbNPs are primarily made of sustainable materials. The EbNP surface-active functionalization agent can be released more easily increasing the efficiency of the agent. Surface property modification e.g. to protect the active agent, to alter the release properties of the active agent, to change the stability of the system, to alter attractive or repulsive forces to a specific target, to change the charge or hydrophobicity of the system, and to prepare the system for further functionalization and/or modification serve as further possibilities to optimize the efficiency of the EbNPs. As a result, functionalized EbNPs use in general significantly smaller amounts of active agent to deliver the same functionality than their persistent counterparts.
- Additional Safety: Hazardous risks associated with persistent nanoparticle waste have been recognized by the Environmental Protection Agency (EPA)[30, 31]. Other than persistent nanoparticles exhibiting post utilization hazards for humans and the environment, due to nanoparticle migration, accumulation, and activity, functionalized EbNPs increase nanomaterial safety as they will deplete rendering the particles benign, which biodegrade after their intended use minimizing any hazardous effects stemming from nanomaterial waste.
- Formulation novelty: Choice of materials in functionalized EbNPs results in specific novel ingredient formulations.
- Application novelty: Persistent nanoparticle systems have limited application potential. The benign nature (by design) of the invention opens usage opportunities in markets closed for persistent nanoparticles, which can be found in the multibillion pesticide, food, and drug industries.

Functionalized EbNPs consisting of a core, one or more functionalizing agents, and one or more surface modifiers, whose details are outlined in the definition of terms, could be based on the following combination of materials. The EbNP core consists mainly of biopolymers or a combination of biopolymers from the group of modified lignin, modified cellulose, hemi or lingo cellulose, modified chitosan, modified chitin, prolamines, and gluten. Most preferable lignins are modified lignins extracted via Kraft pulping process including sulfonated (INDULIN C lignin) and unsulfonated lignin (INDULIN AT lignin) from MeadWestvaco and others, and extracted via organosolv process such as High Purified Lignin (HP-L™) from Lignol. Preferable modified lignins include Kraft pulping lignin extracted via Lignoboost process from Metso, and their derivatives. Most preferable modified celluloses include hydroxyl propyl methyl cellulose phthalate (e.g., HP-55 or HP-55S from Shin-Etsu), hypromellose acetate succinate (e.g., AS-HF from Shin-Etsu), and their derivatives. Other preferable modified celluloses include methyl cellulose, ethyl cellulose, cellulose acetate, hydroxyethyl cellulose, cellulose nitrate, cellulose propionate, and their derivatives. Most preferable modified chitosans include low molecular weight (Mw) chitosans, and their derivatives including chemically modified chitosan with amino groups in the backbone of chitin. Preferable chitosans include medium and high Mw chitosan and their derivatives. The active agent may be any biologically active component. This includes most preferably monovalent and divalent cationic metal ions including biocidal $Ag^+$ and $Cu^{2+}$, biocidal semiconductor compounds such as ZnO and $TiO_2$, and natural and synthetic pesticides. Preferable active agents are amines, biopolymers with biocide activity including low Mw chitosan with amino groups, and synthetic polymers including negatively and positively charged polyelectrolytes. Other possible functionalization agents include the group of hydrophilic and hydrophobic pharmaceuticals, food additives, proteins, peptides, and others. Surface property modifiers are surfactants that include synthetic polymers and biopolymers as defined previously. Most preferably are positively charged biocidal amines such as polydiallyldimethylammonium chloride (PDADMAC) or poyallylamine hydrochloride (PAH), and oils and silicon based surfactants used as pesticide transfer and targeting agents. Other groups of surface modifiers include positively and negatively charged polyelectrolytes for surface charge modification, non-ionic surfactants, protein based surfactants, emulsifiers, and polysaccharides.

Negatively charged hydrophobic EbNPs are synthesized via one of the four suggested green synthesis routes with mean diameters most preferably in the range of 20 to 100 nm. Preferable EbNPs from synthesis may also result in bigger particles with mean diameters typically up to 500 nm, or more. The procedures include the water-water based pH-drop method, the solvent-water based pH-drop method, solvent-antisolvent method, and the polyelectrolyte-addition method. Taking lignin as input material, INDULIN AT lignin (IAT) and HP-L™ nanoparticles have been synthesized by the previously mentioned procedures. Table 7 compares the advantages and limitations of each method. In the water-water based pH-drop method, supersaturation and subsequent nanoparticle formation are achieved upon addition of acid to dissolved lignin in water at elevated pH to drop the pH into the range of pH 1.5 to 3.0. The pH stability can be increased upon adsorption of positively charged polyelectrolytes most preferably with PDADMAC, PAH, and others on the negatively charged EbNP surface. In the organic solvent-water based pH drop method, lignin is first dissolved in organic solvent such as ethylene glycol, toluene, or similar. Supersaturation is reached upon addition of acid precipitating out negatively charged hydrophobic EbNPs. The EbNPs formed in organic media may be transferred into water via dialysis or dilution. In the solvent-antisolvent method, biopolymer is dissolved in solvent such as acetone or ethanol. Supersaturation is reached upon rapid addition of antisolvent such as water precipitating out negatively charged hydrophobic EbNPs. In the polyelectrolyte-addition method, biopolymer is dissolved in solvent, typically water at adjusted pH. EbNPs are formed upon addition of positively charged polyelectrolytes. In comparison to prior art, each of the four green synthesis routes is performed at room temperature without crosslinking reaction. This differs significantly from the methods reported in patent literature in which chemically modified cross-linked lignin nanoparticles were synthesized at elevated temperatures[32, 33]. While chemically modified lignin nanoparticles may not biodegrade as easily, other advantages of the green synthesis methods described include utilization of inexpensive materials, low hazard potential, room temperature operations and therefore no need for external energy input or cooling, size control, scalability, and short synthesis times from prepared stock solutions to synthesized EbNPs in the minute range. According to the advantages outlined, the EbNP synthesis costs are low.

The second part of the invention includes nanoparticle functionalization in order to infuse the matrix with an active ingredient or otherwise create the desired usage characteristics. Functionalization methods of the EbNP carrier include infusion, and absorption and/or physical and chemical adsorption of active agent. Both weak and strong binding of the active agent are possible mechanisms involved in the functionalization. This binding of the agent can occur because of electrostatic interaction, hydrophobic or hydrophilic interactions, reduction processes, chemical linking, kinetic and entropy driven capture of the functional molecules. In comparison to persistent nanoparticle systems compromised of the active agent alone, the functionalized EbNP technology suggests higher efficiency in terms of optimized smaller amount of active agent used to deliver the same functionality ultimately minimizing risks and hazards stemming from excess active agent.

The adjustment and customization of the surface properties is used to replicate and enhance the particle properties needed for its functionality, and can be achieved by introducing one or more modifiers on the EbNP surface. Depending on the surface modifier chosen, the binding strength and the adsorption processes can vary accordingly. Surface properties that are controlled on this stage include surface charge, pH stability, hydrophobicity, biocidal activity, and others. Changes in surface properties can specifically be performed for better particle targeting, to increase the shelf life of the system, to alter the colloidal stability, to modify the interaction potential with the environment or a specific target, to protect the active agent, to customize depletion and transport effects of active agent, and others.

Applications:

The EbNP systems suggested in the present invention can find applications in different areas of technology and industrial products. The key new element is that the functionalized EbNPs may be designed to exhibit locally confined and temporarily limited bioactivity, by delivering the same desired activity as permanent nanoparticles currently employed in various applications, but only during the time of their application. Since functionalized EbNPs can be engineered to have complete functional equivalency to a variety of permanent hazardous nanoparticles, EbNPs may therefore replace a wide range of metal or semiconductor nanoparticles employed at moderate temperatures.

Besides these multimillion dollar applications, the benign nature of the invention opens opportunities for its use in markets presently closed for persistent nanoparticles. New additional applications may be found in the multibillion pesticide, food, and drug industries. Applications of functionalized EbNPs are sectioned in immediate applications, new applications, and new applications with FDA approved EbNP matrix.

Immediate applications of these new particles include/invention can be employed as:

a) Functionalized environmentally benign nanoparticles (EbNPs) with antimicrobial properties to be used as additive to detergents or soaps to establish or increase the antimicrobial, antifungal, or antiviral function of the product.

b) Surface coatings made of biodegradable components consisting of modified lignin and/or modified cellulose, hemicellulose or chitin functionalized with positively charged polyelectrolytes and/or $Ag^+$ ions adsorbed in/on the matrix for antimicrobial, antifungal, and antiviral surface functionalization in consumer products.

c) Functionalized EbNP suspensions for dipping or spraying with added modified lignin and/or modified cellulose, hemicellulose or chitin in diameters ranging from 20 to 500 nm, optionally functionalized with positively charged polyelectrolytes, and/or Ag ions adsorbed on the particles, in water-based or organic solvent-based solution, for antimicrobial, antifungal, and antiviral functionalization of surfaces.

d) Functionalized EbNPs consisting of modified lignin and/or modified cellulose, hemicellulose or chitin in diameters ranging from 20 to 500 nm functionalized with positively charged polyelectrolytes and/or Ag ions adsorbed on the particles to be incorporated in/adsorbed on general available water filtration matrixes to provide antimicrobial, antifungal, and antiviral water treatment in addition to basic water filtration.

e) EbNPs consisting of modified lignin and/or modified cellulose, hemicellulose or chitin in diameters ranging from 20 to 500 nm functionalized with biocidal agents such as $Ag^+$, $Cu^{2+}$, or iron oxides coated with positively charged polyelectrolyte incorporated in/adsorbed on general available water filtration matrixes to provide antimicrobial, antifungal, and antiviral water treatment in addition to basic water filtration.
f) Functionalized EbNPs to be used as general active agent carrier system specifically to substitute silicon based particle systems used in the pesticide and food industry.
g) EbNPs functionalized with pesticides and coated with pesticide transfer agent to be used as benign pesticide agent carrier and delivery system with engineered temporal activity to reduce the amount of active agent used and therefore any negative environmental impact while delivering the same functionality, and to increase product safety for humans.

h) Functionalized EbNPs in diameters ranging from 20 to 500 nm functionalized with positively charged polyelectrolytes and/or $Ag^+$ ions adsorbed on the particles to be incorporated in and/or adsorbed on general types of water filtration matrixes to provide antimicrobial, antifungal, and antiviral water treatment in the pharmaceutical industry.

i) Nano-carriers made of biopolymers in diameters ranging from 20 to 500 nm functionalized with positively charged polyelectrolytes and/or $Ag^+$ ions adsorbed on the particles to be incorporated in and/or adsorbed on general types of water filtration matrixes to provide antimicrobial, antifungal, and antiviral water treatment in the food industry.

j) EbNPs in diameters ranging from 20 to 500 nm functionalized with biocidal agents such as $Ag^+$, $Cu^{2+}$, or iron oxides coated with positively charged polyelectrolyte incorporated in/adsorbed on general available water filtration matrixes to provide antimicrobial, antifungal, and antiviral water treatment in addition to basic water filtration.

k) EbNPs functionalized with active agent to be used as general active agent carrier system specifically to substitute silicone-based particle systems used in the pesticide industry.

l) EbNPs functionalized with pesticides and coated with pesticide transfer agent to be used as benign pesticide agent carrier and delivery system with engineered temporal activity to reduce the amount of active agent used and therefore any negative environmental impact while delivering the same functionality, and to increase product safety for humans.

m) EbNPs functionalized with organic pesticides and coated with pesticide transfer agent to be used as benign pesticide agent carrier and delivery system with engineered temporal activity to reduce the amount of active agent used and therefore any negative environmental impact while delivering the same functionality, and to increase product safety for humans.

n) EbNPs functionalized with antimicrobial agent to be used as benign antimicrobial agent carrier and delivery system with engineered temporal activity to combat bacterial and fungal plant pathogens to reduce vegetable spoilage.

o) EbNPs functionalized with antimicrobial agent to be used to functionalize dressings and tampons with antimicrobial effect to decrease the potential of infections.

p) EbNPs functionalized with antimicrobial agent to be used to functionalize an article of hygiene with antimicrobial properties to decrease the potential of infections.

q) EbNPs functionalized with antimicrobial agent to be used to functionalize paper with antimicrobial properties to decrease the potential of infections.

New applications include:

r) EbNPs consisting of modified lignin and/or modified cellulose, hemicellulose or chitin in diameters ranging from 20 to 500 nm, optionally functionalized with positively charged polyelectrolyte, to be used as adsorption matrix for monovalent and divalent hazardous metal ions and hydrophobic agents in liquid-based environmental remediation processes.

s) Process of making EbNPs consisting of modified lignin synthesized via solvent-antisolvent (where water could be both solvent and anti-solvent) process from organosolv lignin, or synthesized via pH drop method in organic solvent or water, or synthesized via addition of negatively charged polyelectrolyte to lignin dissolved in solvent, and/or modified cellulose synthesized via pH drop method in organic solvent or water, or synthesized via addition of negatively charged polyelectrolyte to cellulose dissolved in solvent, in diameters ranging from 20 to 500 nm, optionally functionalized with positively or negatively charged polyelectrolyte, to be used as environmentally benign fillers and protectors in paints in the micro and nano size range in wood constructions.

t) EbNPs functionalized with biocides to be used as paint additive to decrease susceptibility of growth of prokaryotic or eukaryotic cells on the surface.

u) EbNPs functionalized with biocides to be used as additives in sound or heat isolation materials or fillers to decrease susceptibility of growth of prokaryotic or eukaryotic cells on the surface or in the bulk of such materials.

v) Hydrophobic EbNPs with optional biocidal functionalization to be used in wood protection and/or as paint additive to decrease both the wettability of the product and the growth of prokaryotic and eukaryotic cells on the surface of wood products to increase their lifetime.

w) EbNPs to be used as binder additive into paints, ceramics, glues, or coating materials dispersed in the product to serve as linker between the components upon drying increasing the stability of the product.

x) Functionalized EbNPs to be gathered in porous particles frits to serve as catalyst facilitating chemical reactions.

y) EbNPs functionalized with catalytic metals such as Pt or Pt alloys immobilized in porous frits to serve as catalysts facilitating chemical reactions.

z) Functionalized EbNPs with surface coating with specific adsorption potential to serve as adsorption material for targeted biomolecules to be used in biosensor applications.

aa) Bioassays using EbNPs with possibly additional marker or dye functionalization with surface coating exhibiting adsorption potential to specific biopolymers to be used in biomolecular screening applications.

bb) Functionalized EbNPs to be used on bioassay microchip to serve as biomolecule specific adsorption material.

cc) Functionalized EbNPs consisting of synthesized EbNPs and at least one polyelectrolyte to be used as coating material to alter surface properties including hydrophobicity, surface charge, and optional anisotropy.

dd) Foam or emulsion based products, where bubbles or droplets are fully or partially stabilized with EbNPs, having at least one of the additional functionalities as described above, where the additional functionality of the particles is boosted (in terms of dose or efficiency) due to their attachment of the interface and their benign properties further improved when these foams or emulsions are destabilized.

New therapeutic or nutraceutical applications (possibly for FDA-approved or other regulatory approval) of EbNPs described herein include:

ee) Functionalized EbNPs with biocide functionalization to be employed as coating material in food containers, bottles, or cans to decrease antimicrobial or antifungal contamination potential to protect the food from subsequent spoiling.

ff) Functionalized EbNPs with biocide functionalization to be used as food additive to increase the shelf life through making the food less susceptible for bacterial or fungal contamination, and to decrease spreading of bacteria and fungi in the product.

gg) Functionalized environmentally benign nanoparticles consisting of modified lignin and/or modified cellulose, hemicellulose or chitin in diameters ranging from 20 to 500 nm to adsorb hydrophobic drugs and beneficial cationic ions and molecules prior to optional protective functionalization with positively and negatively charged polyelectrolytes to be used as transport agent in oral drug delivery.

hh) Functionalized EbNPs with antimicrobial properties added as active agent in disinfecting and cleaning solutions for soft and rigid contact lenses to protect the eyes of the contact lens wearer from infections.

ii) Functionalized EbNPs with insecticide, herbicide, or fungicide functionalization to be employed as pesticide in the agriculture sector to protect the pesticide from dilution and depletion, to specifically target the pest, and to increase the pesticide concentration locally at the target while decreasing the overall average exposure of pesticide on the protected good.

jj) EbNPs with marker or dye functionalization to be employed as a diagnostic or an indicator for exposure routes in humans, animals, and the environment in general to protect the marker from dilution and depletion, to decrease the overall indicator concentration while using a benign matrix.

kk) EbNPs functionalized with antibiotics to be delivered in humans, animals, and the environment in general to protect the agent from dilution, depletion, and degradation, to decrease the overall antibiotic exposure concentration while using a benign matrix.

ll) EbNPs with Ag infusion to be used as wound dressing, and immobilized antibacterial, antifungal, anti-inflammatory active agent on material used as wound cover.

mm) EbNPs with Ag infusion to be incorporated in hydrogels to provide wound dressing with antibacterial, antifungal, and anti-inflammatory properties.

nn) Functionalized EbNPs with antimicrobial agents to be used as coating materials of catheters including catheters used in neurosurgery for cerebrospinal fluid drainage to reduce the risk of infection.

oo) Functionalized EbNPs with antimicrobial agents to be used as additive to bone cement and implantable materials to reduce risks of infections.

pp) Ag functionalized EbNPs with beneficial properties towards treatment of dermatitis to be used as in cures resulting in reduction of dermatitis due to Ag ions stemming from EbNP system.

qq) Ag functionalized EbNPs with beneficial properties towards treatment of acne resulting to be used in acne treatment solutions in reduction of acne due to Ag ions stemming from EbNP system.

rr) Functionalized EbNPs with antimicrobial properties to be used in urology as coating material for surgical mesh to provide protection towards bacterial infections for pelvic reconstruction.

ss) Functionalized EbNPs (in one non-limiting embodiment, $Ag^+$) with antiviral properties to be used as virus replication inhibitor in direct virus treatments, and in vaccines.

tt) EbNPs functionalized with bactericidal and antifungal agents to be used as preservatives in vaccines to protect the vaccine agent from contamination and therefore, the person vaccinated from infections related to contaminations.

uu) EbNPs functionalized with bactericidal and antifungal agents to be used as coating material in vials, vessels, or syringes holding vaccines to protect the vaccine agent from contamination and therefore, the person vaccinated from infections related to contaminations.

DEFINITION OF TERMS

Biopolymers include linear, branched, or cross-linked biopolymers of natural or technical origin (i.e. physically or chemically modified during processing of natural compounds and appearing usually as bi-product or waste stream of such process)

Biopolymers include large molecular weight natural or technical polyphenols or natural phenolic polymers like lignin or modified lignin or a combination thereof.

Biopolymers from natural or technical origin include physically or chemically modified biopolymers during processing of natural compounds that appear usually as bi-product or waste stream of such process.

Biopolymers include byproducts of degradation of lignin, such as humic acid and others.

Organic solvents include acetone, ethylene glycol, propylene glycol, glycerol, methyl acetate, ethyl acetate, methanol, ethanol, hexanol, petrol ether, toluene, benzene, turpentine, dichlormethane, chloroform, formic acid, isopropanol, polyethylene oxide, and others.

Prolamines include gliadin from wheat, hordein from barley, secalin from rye, zein from corn, kafirin from sorghum or avenin from oats.

Gluten include gladin and glutenin

Cationic metal ions include $Ag^+$, $Ag^{2+}$, $Cu^{2+}$, $Ni^{2+}$, $Co^{2+}$, $Fe^{2+}$, others, and their complexes; precursor of metal ions for e.g., $Ag^+$ are salts such as $AgNO_3$.

Anionic ions include anionic antimicrobial peptides and proteins (AAMPs).

Cytotoxic agents include but are not limited to antibacterial agents such as antibacterial peptides or proteins. Examples include, but are not limited to, bactericidal/permeability-increasing protein (BPI); helical linear peptides, e.g., gramicidin, magainins, melittin; or β-sheet or cyclic peptides such as defensins, amphotericins and nystatin.

Semiconductors include ZnO, ZnSe, ZnS, ZnTe, CuCl, $Cu_2S$, CuO, $TiO_2$, CdSe, CdS, CdTE FeO, $Fe_3O_4$, (α,β,γ,ε), $Fe_2O_3$, $Fe_2S$, NiO, $Ag_2S$, and others.

Pesticides include algaecides, avicides, bactericides, fungicides, insecticides, miticides, molluscicides, nematicides, rodenticides, glyphosate, and virucides.

Amines include primary, secondary, tertiary, and quarternary structures. This includes polydiallyldimethylammonium chloride (PDADMAC), poyallylamine hydrochloride (PAH), polyethyleneimine (PEI), branched polyethyleneimine (BPEI), polyethoxylated tallow amine (POEA), and others.

Non-ionic surfactants include alcohol ethoxylates, alcohol ethoxyfulfates, and others.

Silicon based surfactants include silicone and silicone blends with polysiloxane chains, and include commercial products such as Sylgard® 309 (Wilbur-Ellis Company), Freeway® (Loveland Industries), Dyne-Amic® (Helena Chemical Company), and Silwet L-77® (Loveland and Helena), and others.

Oils include vegetable oil, methylated vegetable oil, seed oils, crop oils, petroleum based oils, silicon based oils, and blends of these. Commercial products include MSO® Concentrate Methylated Seed Oil (Loveland Industries), Hasten® (Wilbur-Ellis Company), Improved JLB Oil Plus (Brewer International), Cide-Kick and Cide-Kick II (Brewer International), Syl-tac™ (Wilbur-Ellis Company), Phase™ (Loveland Industries), Agri-dex® (Helena Chemical Co. or Setre Chemical Co.), Red-Top Mor-Act® (Wilbur-Ellis Company), and others.

Other surface modification and activation agents include amphiphilic proteins, soy proteins, proteins, DNA, fluorescence DNA, peptides, fluorescence markers, amino acids, and others.

optimal amount of silver in the form of adsorbed $Ag^+$ ions. The active $Ag^+$ ions are released only during the targeted adsorption of the polyelectrolyte-coated particles onto bacterial targets. We have shown that the bactericidal action of these silver-loaded, surface functionalized particles exceeds the one of the common Ag nanoparticles and that the new EbNPs are capable of killing a broad spectrum of microbes. A more detailed description of these preliminary results is provided in the main section of this document. The nanoparticles will become depleted of $Ag^+$ ions shortly after use rendering the nanosystem benign. If the EbNPs are released in the environment concerns related to nanowaste toxicity are minimized as the particles will degrade, for they are made from natural biopolymers. Both the nanoparticles and the processes for their fabrication are simple and inexpensive. This approach is not limited only to bactericidal silver ions as active agent, but can be applied to the development of many new biopolymer particles with antiviral, antifungal, antitoxin, anticancer, chemical decontamination and other functionalities.

Background.

Engineered nanoparticles are in use or being considered for use across a wide range of fields. However, lingering concerns about the potential health hazards of nanoparticles and their accumulation in the environment have limited the expansion of nanoparticle technology into many medical, environmental, and military applications. Silver nanoparticles (AgNPs) have emerged as the most widely employed persistent nanoparticles (PNPs), as their broad-spectrum antimicrobial properties allow them to combat bacteria strains exhibiting antibiotic resistance,[11] which are reported in human pathogens including *Escherichia coli* (*E. coli*)[12], *Pseudomonas aeruginosa* (*P. aeruginosa*)[13], and others. Furthermore, AgNPs are effective agents against viruses (e.g. herpes), spores (e.g., anthrax), and fungi (e.g. *Candida albicans*)[34]. Such broad-spectrum biocidal agents can minimize the potential for nosocomial infections[15] in applications including antimicrobial wound dressings, textiles,[20] and water filters.[21] However, toxicity studies on AgNPs in contact with skin, specifically in commercially available wound dressings, indicate that AgNP containing solutions exhibit stronger cytotoxic effects toward keratinocytes than do PNP free counterparts.[23] In addition, in vitro studies on mammalian fibroblasts have revealed that AgNP can induce apoptosis.[24, 25] In this context, AgNP may potentially affect human health.[26]

TABLE 7

Green synthesis methods comparison table.

| Method | EbNP material | d [nm] | pH-stability | Main parameters for particle size control | Advantage | Limitations |
|---|---|---|---|---|---|---|
| water-water pH-drop | IAT, HP-L ™ | 20-200(+) | 1.8-3.0 | increasing pH-drop magnitude results in bigger particles<br>higher initial wt % results in bigger particles | completely water based | size control at target pH<br>pH stability (can be overcome)<br>native EbNPs not suitable for infusion with active agent |
| organic solvent-water pH-drop | IAT | 20-500 | 3.0-10.0 | increasing pH-drop magnitude results in bigger particles<br>higher initial wt % results in bigger particles | pH stability<br>size control<br>physical adsorption of cations possible | organic solvent residues (can be minimized relatively easy) |
| solvent-antisolvent | HP-L ™ | 20-200(+) | 3.0-10.0 | increasing dilution rate with antisolvent results in smaller particles<br>higher initial wt % results in bigger particles | pH stability<br>size control | organic solvent residues (can be minimized)<br>physical adsorption of cations limited |
| polyelectrolyte addition | IAT, HP-L ™ | 20-200(+) | 3.0-10.0 | ratio lignin to polyelectrolyte influences particle size and surface charge | completely water based | native EbNPs not suitable for infusion with active agent |

Section 3

Executive Summary.

One of the most widely used classes of nanomaterials today is the silver nanoparticles (AgNPs), which exhibit general antimicrobial, antisporal and antifungal activity, while being of low toxicity to humans. The application of Ag nanoparticles, however, has met a number of serious problems, due to their relatively large cost and the rapidly growing concerns about the environmental and human dangers by the persistent nanoparticles released post application. We have pioneered a set of new ideas that resulted in the demonstration of a novel class of functionalized, environmentally-benign, nanoparticles (EbNPs) as highly efficient microbicidal substitutes of the AgNPs (FIG. 24). These particles are made of biodegradable and environmentally benign biopolymers such as lignin, and are infused with an The environmentally benign nanoparticles (EbNPs) that we have developed address these safety concerns associated with nanosystems without sacrificing the powerful nanoscale functionality. Biopolymers such as lignin serve as suitable matrix for benign nanoparticle systems. Lignin is the most abundant aromatic polymer in nature,[4] has an amorphous structure, and is biodegradable. Matrixes of INDULIN AT lignin (IAT), depicted in FIG. 25, have shown high adsorption capabilities of heavy metal ions for environmental remediation purposes. In these applications, cationic metal ions are electrostatically attracted to IAT, which is negatively charged due to deprotonation of its main functional groups.[8,9] Recently, we reported the synthesis of pH-stable IAT-based environmentally biodegradable nanoparticles in ethylene glycol by a process that is simple, predominantly water-based, and does not include harsh organic solvents or chemical agents.[35]

Figure 25:
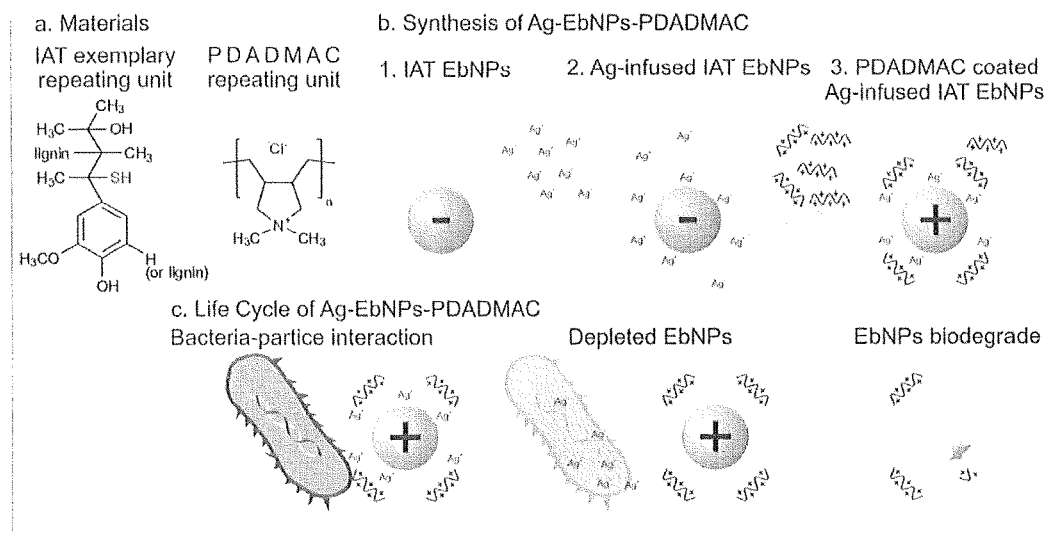
FIG. 25: Schematic of the concept for making and using functionalized EbNPs. a, Repeating units of material building blocks. b, Synthesis steps for making functionalized EbNPs. c, Life cycle of EbNPs—application and post-utilization activity.

We further proved that by infusing IAT EbNPs with functional metal ions, such as antimicrobial silver ions, and additional surface modification, such as switching the surface charge from negative to positive, it is possible to synthesize degradable nanoparticles that match the nanoparticle functionality of their respective PNPs, while increasing utilization and post-utilization safety. The schematic in FIG. 25 shows the three steps involved in generating sustainable antimicrobial EbNPs. First, we synthesize negatively charged IAT EbNPs suitable for functionalization with cationic metal ions. In the next step, we adsorb antimicrobial silver ions from water solution of silver nitrate. Finally, we reverse the surface potential of the particles from negative to positive via adsorption of a positively charged polyelectrolyte. We use a relatively benign multifunctional cationic polyelectrolyte, polydiallyldimethylammonium chloride [PDADMAC] as illustrated in FIG. 25, which has been frequently employed in environmental applications such as water treatment, in consumer products such as cosmetics, and in biological application including insecticides and algaecides.[36] Besides the surface charge modification, the PDADMAC layer may protect the particle system from unintended $Ag^+$ ion depletion. In addition, as quarternized amines are known to exhibit antimicrobial effects, thus PDADMAC may potentially increase the antimicrobial efficiency of the EbNPs.[37] Hence, the antimicrobial EbNPs (Ag-EbNPs-PDADMAC) with functional equivalency to AgNPs consist of (1) a biodegradable EbNP core, (2) highly antimicrobial silver ions as active agent, and (3) a surface charge modifier. At contact with the cells, the particles can release antimicrobial silver ions, which can be transfer into the cell, to perform the desired antimicrobial function leading to bacteria cell death. In contrast to the metallic silver in AgNPs, silver in Ag-EbNPs-PDADMAC is already available in its ionic form and therefore, may be transferred to the cell more readily. This process may result in rapid silver ion depletion of the Ag-EbNPs-PDADMAC system. At the end of the lifecycle, the Ag-EbNPs-PDADMAC system, which is depleted of silver ions, is rendered inactive and will degrade over time.

Antimicrobial Testing and Comparison of AgNPs with Silver-Infused EbNPs.

We compared the antimicrobial activity of Ag-EbNPs-PDADMAC with the one of positively charged branched polyethylene imine AgNPs (BPEI AgNPs) and $AgNO_3$ solutions, We performed quantitative antimicrobial tests on Gram-negative E. coli BL21 (DE3), a common human pathogen, and qualitative tests on Gram-negative P. aeruginosa, a human pathogen not susceptible to antimicrobial amines such as BPEI and PDADMAC. Therefore, any antimicrobial activity in the P. aeruginosa tests will predominantly stem from silver. The testing procedure are reported in Section 1.

Figure 26:
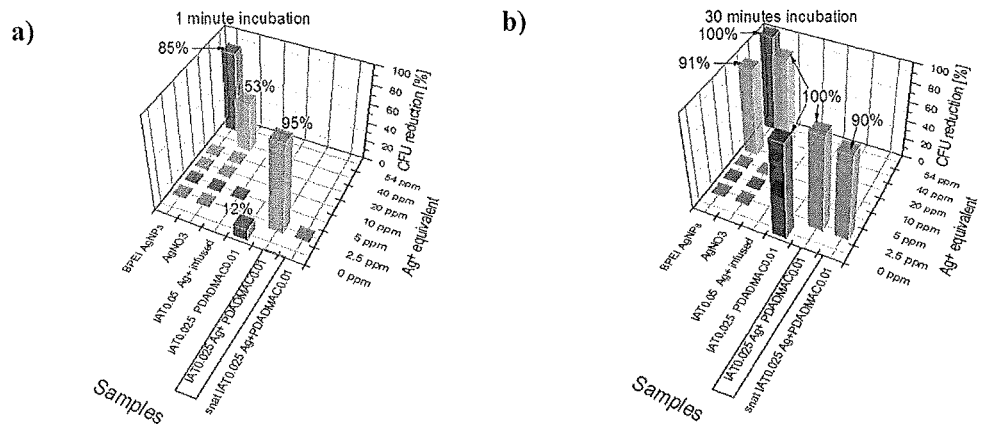
FIG. 26: Qualitative *E. coli* test—CFU reduction efficiency of selected IAT EbNP, BPEI AgNP, and $AgNO_3$ samples. a, after 1 minute contact time. b, after 30 minutes contact time.

The quantitative antimicrobial efficiencies of each active agent in the E. coli tests are compared in FIG. 26. The microbicidal efficiency of six different samples with increasing Ag ppm equivalent ranging from 0 ppm to 54 ppm was investigated. The graphs show the reduction efficiency at two time points, 1 minute and 30 minutes. The weight percentages of the control samples and the silver contents in the active agents were chosen to show antimicrobial thresholds and to facilitate comparisons between the samples. Native IAT EbNPs without $Ag^+$ functionalization and surface modification did not result in any observable reductions in CFU (not reported), which suggests that the native IAT EbNPs are benign. Also, IAT EbNPs loaded with $Ag^+$ but without PDADMAC coating did not result in significant reduction of CFU after 1 minute (0%) and 30 minutes (5%). We believe that the low antimicrobial efficiency may be contributed to the negative surface charge of these EbNPs, which may hinder them from overcoming the electrostatic barrier between the particles and the bacteria. IAT EbNPs coated with PDADMAC resulted in strong reduction of CFU after an exposure time of 30 minutes, which may be attributed to the antimicrobial effect of the quarterly amine PDADMAC. The Ag+-loaded and surface-functionalized sample, Ag-EbNPs-PDADMAC, exhibited strong reduction in CFU, prevalent after 1 minute exposure time. The corresponding supernatant of Ag-EbNPs-PDADMAC exhibited no observable effect after 1 minute. BPEI AgNPs and $AgNO_3$ solutions exhibited antimicrobial effects at 20 ppm Ag and 40 ppm Ag respectively. Overall, the Ag-EbNPs-PDADMAC sample outperformed the BPEI AgNPs and $AgNO_3$ samples in terms of antimicrobial efficiency normalized on Ag ppm equivalent.

TABLE 8

Comparison of conventional AgNPs with the new silver-infused EbNPs.

| Parameter | Silver Nanoparticles (AgNPs) | New functionalized EbNPs |
|---|---|---|
| Broad spectrum antimicrobial/ antisporal/ antiviral agent | Yes | Yes |
| Efficiency | ++ | +++ (up to 10X higher efficiency) |
| Silver-content (priority pollutant) | High | Low (reduction factor up to 10) |
| Matrix | Persistent (metallic Ag based) | Degradable (biopolymer-based) |
| Suitability for customized functionality | Low (one function) | High (functionalization with other active agents possible) |
| Regulatory Concerns | Yes (under scrutiny by US EPA) | Minimized (collaboration with EPA) |
| Comparative activity towards | Medium (tested at US EPA) | Low (tested at US EPA) |

TABLE 8-continued

Comparison of conventional AgNPs with the new silver-infused EbNPs.

| Parameter | Silver Nanoparticles (AgNPs) | New functionalized EbNPs |
|---|---|---|
| mammalian cells | | |
| Bioactivity post-utilization | Yes (metallic core remains active) | Minimized (depleted of active agent) |
| Scalability | Difficult (mostly batch production) | Yes (continuous flow production possible) |
| Comparative concentration [wt %] in solution | Low | High (10 to 100 higher) |
| Price | $400/g AgNPs in solution (estimate, PlasmaChem GmbH, 2012) | $4.0/g EbNPs in solution (conservative estimate) |

Figure 27:
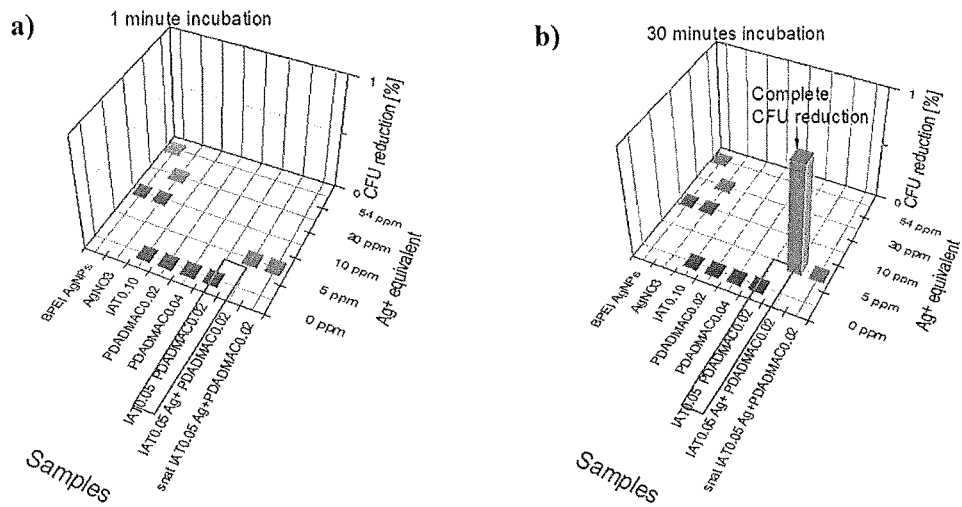
FIG. 27: Quantitative *Pseudomonas aeruginosa* test—CFU reduction efficiency of selected IAT EbNP, BPEI AgNP, and $AgNO_3$ samples. a, after 1 minute contact time. b, after 30 minutes contact time.

As mentioned above, the qualitative antimicrobial test on P. aeruginosa can distinguish the antimicrobial effect of PDADMAC from the effect of silver (FIG. 27). BPEI AgNPs and AgNO$_3$ solutions exhibited no complete antimicrobial effect after 30 minutes incubation time. The control sample IAT EbNP and the IAT EbNPs coated with PDADMAC also did not result in any significant effect. Thus, the sample Ag-EbNPs-PDADMAC was the only one that exhibited complete or 100% antimicrobial efficiency after 30 minutes. The supernatant of the sample Ag-EbNPs-PDADMAC did not show any antimicrobial effect after 30 minutes of incubation time. The results suggest that the antimicrobial action of Ag-EbNPs-PDADMAC is delivered by silver ions. Comparing all active agents tested in terms of antimicrobial efficiency, we establish that Ag-EbNPs-PDADMAC again proved most effective.

presents a comparison of the properties of common AgNPs with our novel silver-infused EbNPs.

Hypothesis of the Antibacterial Mechanism of Ag-EbNPs-PDADMAC.

Figure 28:
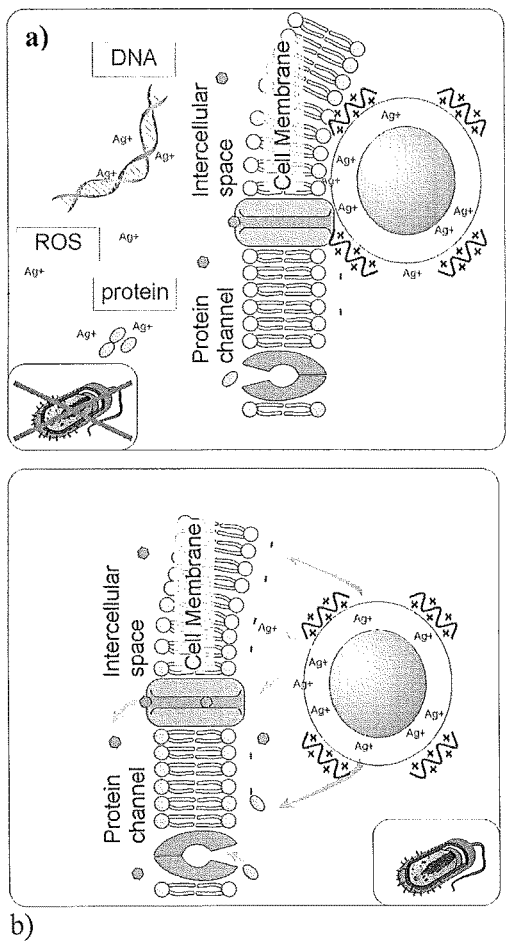
FIG. 28: Schematic of the hypothesis of the antimicrobial mechanism of f-EbNPs-PDADMAC. a, Ag-EbNP-PDADMAC are electrostatically attracted to bacteria cell and b, can deliver the silver ions leading to cell death.

The antibacterial effect of Ag-EbNPs-PDADMAC, is a combinatorial effect of the antimicrobial properties of Ag$^+$ ions and of the quarternized amine PDADMAC. For the bacteria not susceptible for bactericidal amines such as P. aeruginosa,[38, 39] the antimicrobial effect is based on the bactericidal activity of silver-ions. We suggest that the Ag$^+$ ions are weakly bound to the EbNP binding sites and locally concentrated on the EbNP surface. These Ag$^+$ ions may be surface active and could be released upon contact with a bacteria cell membrane. A possible mechanism of the antimicrobial Ag-EbNPs-PDADMAC activity is illustrated in FIG. 28. Ag-EbNPs-PDADMAC particles are electrostatically attracted to the negatively charged bacteria cell membrane, and will eventually adhere to it. As the control sample of EbNPs with PDADMAC but without Ag$^+$ ions did not show antimicrobial effects towards P. aeruginosa, we suggest that the particles by themselves may not destroy the integrity of the cell membrane, which could result in cell lyses and therefore cell death. Hence, we suggest that the antimicrobial effect stems predominately from Ag$^+$ ions, which may be released by the EbNP system towards the bacteria. As the Ag$^+$ ions may eventually migrate into the cell, they could adversely affect bacteria cell functions and therefore, lead to cell death. Conclusions. We developed a new class of microbicidal nanoparticles with increased efficiency and improved post-utilization safety. In contrast to AgNPs, the Ag-EbNPs-PDADMAC system is synthesized via green chemistry and employs degradable, benign and sustainable materials. Since these EbNPs can promote significantly higher antimicrobial activities in terms of Ag equivalents in comparison to persistent AgNPs, their environmental footprint is largely reduced. Furthermore, antimicrobial EbNPs are benign towards mammalian cells in comparison to AgNPs at equivalent silver concentration. As the EbNP technology is flexible and may be applied to a wide range of active agents, functionalized EbNPs may be suitable to substitute a wide range of applied metal nanoparticles.

REFERENCES

Section 2 and 3

1. Bystrzejewska-Piotrowska, G.; Golimowski, J.; Urban, P. L., Nanoparticles: Their potential toxicity, waste and environmental management. *Waste Management* 2009, 29 (9), 2587-2595.
2. Stern, S. T.; McNeil, S. E., Nanotechnology Safety Concerns Revisited. *Toxicological Sciences* 2008, 101 (1), 4-21.
3. Walser, T.; Limbach, L. K.; Brogioli, R.; Erismann, E.; Flamigni, L.; Hattendorf, B.; Juchli, M.; Krumeich, F.; Ludwig, C.; Prikopsky, K.; Rossier, M.; Saner, D.; Sigg, A.; Hellweg, S.; Gunther, D.; Stark, W. J., Persistence of engineered nanoparticles in a municipal solid-waste incineration plant. *Nat Nano* 2012, advance online publication.
4. Lora, J. H.; Glasser, W. G., Recent Industrial Applications of Lignin: A Sustainable Alternative to Nonrenewable Materials. *Journal of Polymers and the Environment* 2002, 10 (1), 39-48.
5. Iiyama, K.; Lam, T.; Stone, B. A., Covalent Cross-Links in the Cell Wall. *Plant Physiol.* 1994, 104 (2), 315-320.
6. Glasser, W. G.; Barnett, C. A.; Muller, P. C.; Sarkanen, K. V., The chemistry of several novel bioconversion lignins. *J Agr Food Chem* 1983, 31 (5), 921-930.
7. Chakar, F. S.; Ragauskas, A. J., Review of current and future softwood kraft lignin process chemistry. *Industrial Crops and Products* 2004, 20 (2), 131-141.
8. Guo, X.; Zhang, S.; Shan, X.-q., Adsorption of metal ions on lignin. *Journal of Hazardous Materials* 2008, 151 (1), 134-142.
9. Harmita, H.; Karthikeyan, K. G.; Pan, X., Copper and cadmium sorption onto kraft and organosolv lignins. *Bioresource Technology* 2009, 100 (24), 6183-6191.
10. Frangville, C.; Rutkevicius, M.; Richter, A. P.; Velev, O. D.; Stoyanov, S.; Paunov, V. N., Fabrication of Environmentally Biodegradable Lignin Nanoparticles. *Chem. PhysChem* 2012, 13 ((in press)).
11. Panáček, A.; Kvítek, L.; Prucek, R.; Kolář M.; Večeřová, R.; Pizúrová, N.; Sharma, V. K.; Nevěčná, T. j.; Zbořil, R., Silver Colloid Nanoparticles: Synthesis, Characterization, and Their Antibacterial Activity. *The Journal of Physical Chemistry B* 2006, 110 (33), 16248-16253.

12. Cohen, S, N.; Chang, A. C. Y.; Hsu, L., Nonchromosomal Antibiotic Resistance in Bacteria: Genetic Transformation of *Escherichia coli* by R-Factor DNA. *Proceedings of the National Academy of Sciences* 1972, 69 (8), 2110-2114.

13. Poole, K.; Krebes, K.; McNally, C.; Neshat, S., Multiple antibiotic resistance in *Pseudomonas aeruginosa*: evidence for involvement of an efflux operon. *Journal of Bacteriology* 1993, 175 (22), 7363-7372.

14. Carmeli, Y.; Troillet, N.; Karchmer, A. W.; Samore, M. H., Health and economic outcomes of antibiotic resistance in *pseudomonas aeruginosa*. *Archives of Internal Medicine* 1999, 159 (10), 1127-1132.

15. Cohen, M. L., Epidemiology of Drug Resistance: Implications for a Post-Antimicrobial Era. *Science* 1992, 257 (5073), 1050-1055.

16. Samuel, U.; Guggenbichler, J. P., Prevention of catheter-related infections: the potential of a new nano-silver impregnated catheter. *Int J Antimicrob Ag* 2004, 23, Supplement 1 (0), 75-78.

17. Gosheger, G.; Hardes, J.; Ahrens, H.; Streitburger, A.; Buerger, H.; Erren, M.; Gunsel, A.; Kemper, F. H.; Winkelmann, W.; von Eiff, C., Silver-coated megaendoprostheses in a rabbit model an analysis of the infection rate and toxicological side effects. *Biomaterials* 2004, 25 (24), 5547-5556.

18. Ohashi, S.; Saku, S.; Yamamoto, K., Antibacterial activity of silver inorganic agent YDA filler. *Journal of Oral Rehabilitation* 2004, 31 (4), 364-367.

19. Klasen, H. J., A historical review of the use of silver in the treatment of burns. II. Renewed interest for silver. *Burns* 2000, 26 (2), 131-138.

20. Lee, H. J.; Yeo, S. Y.; Jeong, S. H., Antibacterial effect of nanosized silver colloidal solution on textile fabrics. *J Mater Sci* 2003, 38 (10), 2199-2204.

21. Jain, P.; Pradeep, T., Potential of silver nanoparticle-coated polyurethane foam as an antibacterial water filter. *Biotechnol Bioeng* 2005, 90 (1), 59-63.

22. Kulthong, K.; Srisung, S.; Boonpavanitchakul, K.; Kangwansupamonkon, W.; Maniratanachote, R., Determination of silver nanoparticle release from antibacterial fabrics into artificial sweat. *Particle and Fibre Toxicology* 2010, 7 (1), 8.

23. Paddle-Ledinek, J. E. M. S., A. M; Nasa, Zeyad B. Sc; Cleland, Heather J. F.R.A.C.S, Effect of Different Wound Dressings on Cell Viability and Proliferation. *Plastic & Reconstructive Surgery. Current Concepts in Wound Healing.* 2006, 117 (7S).

24. Arora, S.; Jain, J.; Rajwade, J. M.; Paknikar, K. M., Cellular responses induced by silver nanoparticles: In vitro studies. *Toxicology Letters* 2008, 179 (2), 93-100.

25. Arora, S.; Jain, J.; Rajwade, J. M.; Paknikar, K. M., Interactions of silver nanoparticles with primary mouse fibroblasts and liver cells. *Toxicology and Applied Pharmacology* 2009, 236 (3), 310-318.

26. Ahamed, M.; AlSalhi, M. S.; Siddiqui, M. K. J., Silver nanoparticle applications and human health. *Clinica Chimica Acta* 2010, 411 (23-24), 1841-1848.

27. Kumar, A.; Vemula, P. K.; Ajayan, P. M.; John, G., Silver-nanoparticle-embedded antimicrobial paints based on vegetable oil. *Nat Mater* 2008, 7 (3), 236-241.

28. Raveendran, P.; Fu, J.; Wallen, S. L., Completely "Green" Synthesis and Stabilization of Metal Nanoparticles. *J Am Chem Soc* 2003, 125 (46), 13940-13941.

29. Tan, S.; Erol, M.; Attygalle, A.; Du, H.; Sukhishvili, S., Synthesis of Positively Charged Silver Nanoparticles via Photoreduction of AgNO3 in Branched Polyethyleneimine/HEPES Solutions. *Langmuir* 2007, 23 (19), 9836-9843.

30. Hassellöv, M.; Readman, J.; Ranville, J.; Tiede, K., Nanoparticle analysis and characterization methodologies in environmental risk assessment of engineered nanoparticles. *Ecotoxicology* 2008, 17 (5), 344-361.

31. Luoma, S, N., Silver nanotechnologies and the Environment. Woodrow Wilson International Center for Scholars. Washington, D.C., USA 2008, 72.

32. S., M. D. Submicron lignin dispersions. 4957557, 1990.

33. Peter, S. Submicron lignin-based binders for water-based black ink formulations. 5192361, 1993.

34. Jain, K. K., The Handbook of Nanomedicine. Springer: 2012; p 422.

35. Frangville, C.; Rutkevičius, M.; Richter, A. P.; Velev, O. D.; Stoyanov, S. D.; Paunov, V. N., Fabrication of Environmentally Biodegradable Lignin Nanoparticles. *Chem Phys Chem* 2012, 13 (18), 4235-4243.

36. Wandrey, C.; Hernández-Baraj as, J.; Hunkeler, D., Diallyldimethylammonium Chloride and its Polymers. In *Radical Polymerisation Polyelectrolytes*, Capek, I.; Hernfández-Barajas, J.; Hunkeler, D.; Reddinger, J. L.; Reynolds, J. R.; Wandrey, C., Eds. Springer Berlin Heidelberg: 1999; Vol. 145, pp 123-183.

37. Zhao, X.; Zhang, Y., —Bacteria-removing and Bactericidal Efficiencies of PDADMAC Composite Coagulants in Enhanced Coagulation Treatment.—*CLEAN—Soil, Air, Water* 2012, (in press).

38. Adair, F. W.; Geftic, S. G.; Gelzer, J., Resistance of *Pseudomonas* to Quaternary Ammonium Compounds. I. Growth in Benzalkonium Chloride Solution, *Applied Microbiology* 1969, 18 (3), 299-302.

39. Langsrud, S.; Sundheim, G.; Borgmann-Strahsen, R., Intrinsic and acquired resistance to quaternary ammonium compounds in food-related *Pseudomonas* spp. *Journal of Applied Microbiology* 2003, 95 (4), 874-882.

Additional data, examples and embodiments may be found in Appendix A attached to the specification of U.S. provisional patent application No. 61/776,274, filed Mar. 11, 2014, the benefit of which application is claimed by the present application, and the contents of which application are incorporated by reference herein in its entirety.

The article "a" and "an" are used herein to refer to one or more than one (i.e., to at least one) of the grammatical object(s) of the article. By way of example, "an element" means one or more elements.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present invention may suitably "comprise", "consist of", or "consist essentially of", the steps, elements, and/or reagents described in the claims.

The following Examples further illustrate the invention and are not intended to limit the scope of the invention.

It is to be understood that, while the invention has been described in conjunction with the detailed description, thereof, the foregoing description is intended to illustrate and not limit the scope of the invention. Other aspects, advantages, and modifications of the invention are within the scope of the claims set forth below. All publications, patents, and patent applications cited in this specification are herein incorporated by reference as if each individual publication or patent application were specifically and individually indicated to be incorporated by reference.

What is claimed is:

1. A cytotoxic particle comprising:
   (a) a discrete, solid, nanoparticle core wherein said nanoparticle core is comprised of a plant derived lignin;
   (b) a cytotoxic metal ion reversibly bound to the discrete nanoparticle core; and
   (c) a bioadhesive adsorption layer coating the discrete nanoparticle core and the metal ion, wherein said bioadhesive adsorption layer comprises a cationic polymer.

2. The cytotoxic particle of claim 1 wherein the reversibly bound metal ion is $Ag^+$, $Ag^{2+}$, $Ag^{3+}$, $Co^{2+}$, $Cu^{1+}Fe^{3+}Cu^{2+}$, $Fe^{2+}$, $Ni^{2+}$, or $Zn^{2+}$.

3. The cytotoxic particle of claim 1 wherein the cationic polymer is a polyamino polymer.

4. The cytotoxic particle of claim 3, wherein the cationic polymer is a polyamino polymer selected from the group consisting of: branched polyethyleneimine (BPEI), polyallylamine hydrochloride (PAH), polydiallyldimethylammonium chloride (PDADMAC), polyethoxylated tallow amine (POEA), polyethyleneimine (PEI), and polylysine.

5. The cytotoxic particle of claim 1, wherein the cationic polymer comprises primary, secondary, tertiary, or quaternized amine functional group.

6. A coated article comprising a surface wherein at least a portion of the surface is coated with the cytotoxic particle of claim 1.

7. The coated article of claim 6, wherein the coated article is an air filter, an article of clothing, an article of hygiene, a building material, a face mask, a food stuff package, a medical device, or a seed.

8. The coated article of claim 6, wherein the coated article is a bandage, a biological implant, a dressing, a medical scaffold, a surgical instrument, or a wound covering.

9. A cytotoxic particle comprising:
   (a) a discrete nanoparticle core wherein said nanoparticle core comprises a biodegradable lignin;
   (b) a cationic and cytotoxic metal ion reversibly bound to the discrete nanoparticle core; and
   (c) a single layer of polyamino cationic polymer coating the discrete nanoparticle core and the cytotoxic metal ion.

* * * * *